(12) United States Patent
Fine et al.

(10) Patent No.: US 7,560,449 B2
(45) Date of Patent: Jul. 14, 2009

(54) METHODS AND THERAPEUTIC COMBINATIONS FOR THE TREATMENT OF DEMYELINATION

(75) Inventors: Jay S. Fine, Bloomfield, NJ (US); Eric McFee Parker, Scotch Plains, NJ (US)

(73) Assignee: Schering Corporation, Kenilworth, NJ (US)

( * ) Notice: Subject to any disclaimer, the term of this patent is extended or adjusted under 35 U.S.C. 154(b) by 868 days.

(21) Appl. No.: 10/701,244

(22) Filed: Nov. 4, 2003

(65) Prior Publication Data

US 2004/0092500 A1     May 13, 2004

Related U.S. Application Data

(60) Provisional application No. 60/493,318, filed on Aug. 7, 2003, provisional application No. 60/424,165, filed on Nov. 6, 2002.

(51) Int. Cl.
    *A61K 31/33*          (2006.01)
(52) U.S. Cl. ...................................................... 514/183
(58) Field of Classification Search ................... 514/183
    See application file for complete search history.

(56) References Cited

U.S. PATENT DOCUMENTS

| | | |
|---|---|---|
| 2,809,194 A | 10/1957 | Novello |
| 3,108,097 A | 10/1963 | Ugi |
| 3,152,173 A | 10/1964 | Ehrhart |
| 3,267,104 A | 8/1966 | Hermans |
| 3,399,192 A | 8/1968 | Regnier |
| 3,692,895 A | 9/1972 | Nelson |
| 3,716,583 A | 2/1973 | Nakamura |
| 3,781,328 A | 12/1973 | Witte |
| 3,948,973 A | 4/1976 | Phillips |
| 4,072,705 A | 2/1978 | Mieville |
| 4,075,000 A | 2/1978 | Abdulla |
| 4,144,232 A | 3/1979 | Koppel |
| 4,148,923 A | 4/1979 | Giudicelli |
| 4,166,907 A | 9/1979 | Krapcho |
| 4,178,695 A | 12/1979 | Erbeia |
| 4,179,515 A | 12/1979 | Mieville |
| 4,235,896 A | 11/1980 | Mieville |
| 4,239,763 A | 12/1980 | Milavec |
| 4,250,191 A | 2/1981 | Edwards |
| 4,260,743 A | 4/1981 | Bose |
| 4,304,718 A | 12/1981 | Kamiya |
| 4,375,475 A | 3/1983 | Willard |
| 4,443,372 A | 4/1984 | Luo |
| 4,444,784 A | 4/1984 | Hoffman |
| 4,472,309 A | 9/1984 | Kamiya |
| 4,479,900 A | 10/1984 | Luo |
| 4,500,456 A | 2/1985 | Spitzer |
| 4,534,786 A | 8/1985 | Luo |
| 4,564,609 A | 1/1986 | Tamura |
| 4,567,195 A | 1/1986 | Schwarz |
| 4,576,748 A | 3/1986 | Greenlee |
| 4,576,749 A | 3/1986 | Zahler |
| 4,576,753 A | 3/1986 | Kamiya |
| 4,581,170 A | 4/1986 | Mueller |
| 4,595,532 A | 6/1986 | Miller |
| 4,602,003 A | 7/1986 | Malinow |
| 4,602,005 A | 7/1986 | Malinow |
| 4,614,614 A | 9/1986 | Ernest |
| 4,616,047 A | 10/1986 | Lafon |
| 4,620,867 A | 11/1986 | Luo |
| 4,626,549 A | 12/1986 | Molloy |
| 4,633,017 A | 12/1986 | Mueller |
| 4,642,903 A | 2/1987 | Davies |
| 4,654,362 A | 3/1987 | Van Lommen |
| 4,675,399 A | 6/1987 | Miller |
| 4,680,289 A | 7/1987 | Applezweig |
| 4,680,391 A | 7/1987 | Firestone |
| 4,687,777 A | 8/1987 | Meguro |
| 4,739,101 A | 4/1988 | Bourgogne |
| 4,778,883 A | 10/1988 | Yoshioka |
| 4,784,734 A | 11/1988 | Torii |
| 4,794,108 A | 12/1988 | Kishimoto |
| 4,800,079 A | 1/1989 | Boyer |
| 4,803,266 A | 2/1989 | Kawashima |
| 4,814,354 A | 3/1989 | Ghebre-Sellassie |
| 4,834,846 A | 5/1989 | Abramson |
| 4,871,752 A | 10/1989 | Ilg et al. |
| 4,876,365 A | 10/1989 | Kirkup |
| 4,879,301 A | 11/1989 | Umio |

(Continued)

FOREIGN PATENT DOCUMENTS

BE          884722 A      12/1980

(Continued)

OTHER PUBLICATIONS van Heek et al., Diabetes, 50:1330-1335, 2001.*

(Continued)

*Primary Examiner*—San-ming Hui
(74) *Attorney, Agent, or Firm*—Mark W. Russell

(57) ABSTRACT

The present invention provides methods for treating demyelination and associated conditions by administering at least one sterol absorption inhibitor and compositions, therapeutic combinations and methods including: (a) at least one sterol absorption inhibitor; and (b) at least one demyelination treatment which can be useful for preventing or treating demyelination and associated conditions, such as multiple sclerosis.

11 Claims, No Drawings

U.S. PATENT DOCUMENTS

| | | | |
|---|---|---|---|
| 4,895,726 | A | 1/1990 | Curtet |
| 4,925,672 | A | 5/1990 | Gremm |
| 4,937,267 | A | 6/1990 | Holloway |
| 4,939,248 | A | 7/1990 | Yoshioka |
| 4,952,689 | A | 8/1990 | Kawashima |
| 4,961,890 | A | 10/1990 | Boyer |
| 4,983,597 | A | 1/1991 | Yang |
| 4,990,535 | A | 2/1991 | Cho |
| 5,021,461 | A | 6/1991 | Robinson |
| 5,030,628 | A | 7/1991 | Joyeau |
| 5,073,374 | A | 12/1991 | McCarty |
| 5,091,525 | A | 2/1992 | Brennan |
| 5,093,365 | A | 3/1992 | Berge |
| 5,099,034 | A | 3/1992 | Yoshida |
| 5,100,675 | A | 3/1992 | Cho |
| 5,106,833 | A | 4/1992 | Broze |
| 5,110,730 | A | 5/1992 | Edgington |
| 5,112,616 | A | 5/1992 | McCarty |
| 5,120,713 | A | 6/1992 | Mugica |
| 5,120,729 | A | 6/1992 | Chabala |
| 5,130,333 | A | 7/1992 | Pan |
| 5,145,684 | A | 9/1992 | Liversidge |
| 5,157,025 | A | 10/1992 | Aberg |
| 5,162,117 | A | 11/1992 | Stupak |
| 5,178,878 | A | 1/1993 | Wehling |
| 5,188,825 | A | 2/1993 | Iles |
| 5,190,970 | A | 3/1993 | Pan |
| 5,204,461 | A | 4/1993 | Murayama |
| 5,219,574 | A | 6/1993 | Wehling |
| 5,223,264 | A | 6/1993 | Wehling |
| 5,229,362 | A | 7/1993 | Kirst |
| 5,229,381 | A | 7/1993 | Doherty |
| 5,229,510 | A | 7/1993 | Knight |
| 5,260,305 | A | 11/1993 | Dennick |
| 5,278,176 | A | 1/1994 | Lin |
| H1286 | H | 2/1994 | Eisman |
| 5,286,631 | A | 2/1994 | Boeck |
| 5,298,497 | A | 3/1994 | Tschollar |
| 5,306,817 | A | 4/1994 | Thiruvengadam |
| 5,318,767 | A | 6/1994 | Liversidge |
| 5,348,953 | A | 9/1994 | Doherty |
| 5,350,868 | A | 9/1994 | Yoshida |
| 5,358,852 | A | 10/1994 | Wu |
| 5,384,124 | A | 1/1995 | Courtelle |
| 5,385,885 | A | 1/1995 | Gasic |
| 5,399,363 | A | 3/1995 | Liversidge |
| 5,401,513 | A | 3/1995 | Wehling |
| 5,412,092 | A | 5/1995 | Rey |
| 5,429,824 | A | 7/1995 | June |
| 5,446,464 | A | 8/1995 | Feldle |
| 5,461,039 | A | 10/1995 | Tschollar |
| 5,464,632 | A | 11/1995 | Cousin |
| 5,494,683 | A | 2/1996 | Liversidge |
| 5,503,846 | A | 4/1996 | Wehling |
| 5,510,118 | A | 4/1996 | Bosch |
| 5,510,466 | A | 4/1996 | Krieger |
| 5,518,187 | A | 5/1996 | Bruno |
| 5,518,738 | A | 5/1996 | Eickhoff |
| 5,545,628 | A | 8/1996 | Deboeck |
| 5,550,229 | A | 8/1996 | Iwasaki |
| 5,552,160 | A | 9/1996 | Liversidge |
| 5,561,227 | A | 10/1996 | Thiruvengadam |
| 5,563,264 | A | 10/1996 | Kume |
| 5,567,439 | A | 10/1996 | Myers |
| 5,576,014 | A | 11/1996 | Mizumoto |
| 5,587,172 | A | 12/1996 | Cherukuri |
| 5,587,180 | A | 12/1996 | Allen |
| 5,591,456 | A | 1/1997 | Franson |
| 5,593,971 | A | 1/1997 | Tschollar |
| 5,595,761 | A | 1/1997 | Allen |
| 5,607,697 | A | 3/1997 | Alkire |
| 5,612,353 | A | 3/1997 | Ewing |
| 5,612,367 | A | 3/1997 | Timko |
| 5,612,378 | A | 3/1997 | Tianbao |
| 5,618,707 | A | 4/1997 | Homann |
| 5,622,719 | A | 4/1997 | Myers |
| 5,622,985 | A | 4/1997 | Olukotun |
| 5,624,920 | A | 4/1997 | McKittrick |
| 5,627,176 | A | 5/1997 | Kirkup |
| 5,631,023 | A | 5/1997 | Kearney |
| 5,631,365 | A | 5/1997 | Rosenblum |
| 5,633,246 | A | 5/1997 | McKittrick |
| 5,635,210 | A | 6/1997 | Allen |
| 5,639,475 | A | 6/1997 | Bettman |
| 5,639,739 | A | 6/1997 | Dominguez |
| 5,656,624 | A | 8/1997 | Vaccaro |
| 5,661,145 | A | 8/1997 | Davis |
| 5,674,893 | A | 10/1997 | Behounek |
| 5,688,785 | A | 11/1997 | Vaccaro |
| 5,688,787 | A | 11/1997 | Burnett |
| 5,688,990 | A | 11/1997 | Shankar |
| 5,691,375 | A | 11/1997 | Behounek |
| 5,698,527 | A | 12/1997 | Kim |
| 5,698,548 | A | 12/1997 | Dugar |
| 5,703,188 | A | 12/1997 | Mandeville |
| 5,703,234 | A | 12/1997 | Iwasaki |
| 5,709,886 | A | 1/1998 | Bettman |
| 5,718,388 | A | 2/1998 | Czekai |
| 5,728,827 | A | 3/1998 | Thiruvengadam et al. |
| 5,734,077 | A | 3/1998 | Regnier |
| 5,739,321 | A | 4/1998 | Wu |
| 5,744,467 | A | 4/1998 | McKittrick |
| 5,747,001 | A | 5/1998 | Wiedmann |
| 5,753,254 | A | 5/1998 | Khan |
| 5,756,470 | A | 5/1998 | Yumibe |
| 5,759,865 | A | 6/1998 | Bruns |
| 5,767,115 | A | 6/1998 | Rosenblum |
| 5,776,491 | A | 7/1998 | Allen |
| 5,807,576 | A | 9/1998 | Allen |
| 5,807,577 | A | 9/1998 | Ouali |
| 5,807,578 | A | 9/1998 | Acosta-Cuello |
| 5,807,834 | A | 9/1998 | Morehouse |
| 5,808,056 | A | 9/1998 | Amato |
| 5,817,806 | A | 10/1998 | Rossi |
| 5,827,536 | A | 10/1998 | Laruelle |
| 5,827,541 | A | 10/1998 | Yarwood |
| 5,831,091 | A | 11/1998 | Ohmizu |
| 5,843,984 | A | 12/1998 | Clay |
| 5,846,966 | A | 12/1998 | Rosenblum |
| 5,847,008 | A | 12/1998 | Doebber |
| 5,847,115 | A | 12/1998 | Iwasaki |
| 5,851,553 | A | 12/1998 | Myers |
| 5,856,473 | A | 1/1999 | Shankar |
| 5,858,409 | A | 1/1999 | Karetny |
| 5,859,051 | A | 1/1999 | Adams |
| 5,862,999 | A | 1/1999 | Czekai |
| 5,866,163 | A | 2/1999 | Myers |
| 5,869,098 | A | 2/1999 | Misra |
| 5,871,781 | A | 2/1999 | Myers |
| 5,880,148 | A | 3/1999 | Edgar |
| 5,883,109 | A | 3/1999 | Gregg |
| 5,886,171 | A | 3/1999 | Wu |
| 5,919,672 | A | 7/1999 | Homann |
| 5,925,333 | A | 7/1999 | Krieger |
| 5,952,003 | A | 9/1999 | Guentensberger |
| 5,952,321 | A | 9/1999 | Doherty |
| 5,959,123 | A | 9/1999 | Singh |
| 5,972,389 | A | 10/1999 | Shell |
| 5,976,570 | A | 11/1999 | Greaves |
| 5,985,936 | A | 11/1999 | Novak |
| 5,990,102 | A | 11/1999 | Hickey |
| 5,994,554 | A | 11/1999 | Kliewer |
| 5,998,441 | A | 12/1999 | Palkowitz |
| 6,008,237 | A | 12/1999 | Sahoo |

| | | | | | | |
|---|---|---|---|---|---|---|
| 6,027,747 | A | 2/2000 | Terracol | 2003/0013699 A1 | 1/2003 | Davis |
| 6,028,109 | A | 2/2000 | Willson | 2003/0013729 A1 | 1/2003 | Iqbal |
| 6,030,990 | A | 2/2000 | Maeda | 2003/0053981 A1 | 3/2003 | Tartaglia et al. |
| 6,033,656 | A | 3/2000 | Mikami | 2003/0069221 A1 | 4/2003 | Kosoglou et al. |
| 6,040,147 | A | 3/2000 | Ridker | 2003/0105028 A1 | 6/2003 | Ghosal et al. |
| 6,043,257 | A | 3/2000 | Dominguez | 2003/0119428 A1 | 6/2003 | Davis |
| 6,056,975 | A | 5/2000 | Mitra | 2003/0119757 A1 | 6/2003 | Davis |
| 6,057,342 | A | 5/2000 | Fevig | 2003/0119796 A1 | 6/2003 | Strony et al. |
| 6,063,764 | A | 5/2000 | Creasey | 2003/0119808 A1 | 6/2003 | LeBeaut et al. |
| 6,066,653 | A | 5/2000 | Gregg | 2003/0119809 A1 | 6/2003 | Davis |
| 6,071,899 | A | 6/2000 | Hickey | 2003/0153541 A1 | 8/2003 | Dudley |
| 6,074,670 | A | 6/2000 | Stamm | 2004/0092500 A1 | 5/2004 | Fine et al. |
| 6,080,767 | A | 6/2000 | Klein | 2006/0009399 A1 | 1/2006 | Davis et al. |
| 6,080,778 | A | 6/2000 | Yankner | 2006/0069080 A1 | 3/2006 | Veltri |
| 6,084,082 | A | 7/2000 | Ravikumar | | | |
| 6,090,830 | A | 7/2000 | Myers | FOREIGN PATENT DOCUMENTS | | |
| 6,090,839 | A | 7/2000 | Adams | CA | 2253769 | 11/1999 |
| 6,093,812 | A | 7/2000 | Thiruvengadam | DE | 2046823 A | 3/1972 |
| 6,096,883 | A | 8/2000 | Wu | DE | 2521113 A | 3/1976 |
| 6,099,865 | A | 8/2000 | Augello | EP | 0002151 A1 | 5/1979 |
| 6,103,705 | A | 8/2000 | Uzan | EP | 0002151 B1 | 5/1979 |
| 6,110,493 | A | 8/2000 | Guentensberger | EP | 0010299 B1 | 2/1984 |
| 6,117,429 | A | 9/2000 | Bucci | EP | 0179559 A2 | 4/1986 |
| 6,121,319 | A | 9/2000 | Somers | EP | 0199630 A1 | 10/1986 |
| 6,127,424 | A | 10/2000 | Martin | EP | 0264231 A1 | 4/1988 |
| 6,133,001 | A | 10/2000 | Homann | EP | 0266896 B1 | 5/1988 |
| 6,139,873 | A | 10/2000 | Hughes | EP | 0274873 B1 | 7/1988 |
| 6,140,354 | A | 10/2000 | Dax | EP | 0288973 B1 | 11/1988 |
| 6,143,885 | A | 11/2000 | Choi | EP | 0311366 B1 | 4/1989 |
| 6,147,090 | A | 11/2000 | DeNinno | EP | 0333268 A1 | 9/1989 |
| 6,147,109 | A | 11/2000 | Liao | EP | 0337549 A1 | 10/1989 |
| 6,147,250 | A | 11/2000 | Somers | EP | 0365364 A2 | 4/1990 |
| 6,159,997 | A | 12/2000 | Tsujita | EP | 0369686 A1 | 5/1990 |
| 6,162,805 | A | 12/2000 | Hefti | EP | 0375527 A1 | 6/1990 |
| 6,166,049 | A | 12/2000 | Smith | EP | 0199630 B1 | 9/1990 |
| 6,174,665 | B1 | 1/2001 | Dullien | EP | 0401705 A3 | 12/1990 |
| 6,180,138 | B1 | 1/2001 | Engh | EP | 0415487 A2 | 3/1991 |
| 6,180,625 | B1 | 1/2001 | Persson | EP | 0455042 A1 | 11/1991 |
| 6,180,660 | B1 | 1/2001 | Whitney | EP | 0457514 A1 | 11/1991 |
| 6,191,117 | B1 | 2/2001 | Kozachuk | EP | 0461548 A3 | 12/1991 |
| 6,191,159 | B1 | 2/2001 | Pinto | EP | 0462667 A2 | 12/1991 |
| 6,200,998 | B1 | 3/2001 | Sahoo | EP | 0475148 A1 | 3/1992 |
| 6,207,697 | B1 | 3/2001 | Han | EP | 0475755 B1 | 3/1992 |
| 6,207,699 | B1 | 3/2001 | Rothman | EP | 0481671 A1 | 4/1992 |
| 6,207,822 | B1 | 3/2001 | Thiruvengadam | EP | 0482498 A3 | 4/1992 |
| 6,214,831 | B1 | 4/2001 | Yokoo | EP | 0524595 A1 | 1/1993 |
| 6,235,706 | B1 | 5/2001 | Gould | EP | 0337549 B1 | 10/1995 |
| 6,242,605 | B1 | 6/2001 | Raveendranath | EP | 0720599 B1 | 7/1996 |
| 6,245,743 | B1 | 6/2001 | Marlowe | EP | 0457514 B1 | 8/1996 |
| 6,248,781 | B1 | 6/2001 | Jeppesen | EP | 0 753 298 A1 | 1/1997 |
| 6,251,852 | B1 | 6/2001 | Gould | EP | 0793958 A2 | 9/1997 |
| 6,262,042 | B1 | 7/2001 | Cook | EP | 0814080 A1 | 12/1997 |
| 6,262,047 | B1 | 7/2001 | Zhu | EP | 0904781 A2 | 3/1999 |
| 6,262,098 | B1 | 7/2001 | Huebner | EP | 1 036 563 A1 | 9/2000 |
| 6,277,584 | B1 | 8/2001 | Chu | EP | 1048295 A2 | 11/2000 |
| 6,316,029 | B1 | 11/2001 | Jain | FR | 1103113 | 10/1955 |
| RE37,721 | E | 5/2002 | Rosenblum | FR | 2779347 | 12/1997 |
| 6,569,879 | B2 | 5/2003 | Liu et al. | GB | 861367 | 2/1961 |
| 7,053,080 | B2 | 5/2006 | Davis et al. | GB | 902658 | 8/1962 |
| 7,071,181 | B2 | 7/2006 | Davis et al. | GB | 1415295 | 11/1975 |
| 2001/0028895 | A1 | 10/2001 | Bisgaier | GB | 2329334 A | 3/1999 |
| 2002/0006919 | A1 | 1/2002 | Thosar | JP | 136485 | 5/1981 |
| 2002/0039774 | A1 | 4/2002 | Kramer | JP | 028057 | 10/1981 |
| 2002/0049222 | A1 | 4/2002 | Yang et al. | JP | 180212 | 3/1986 |
| 2002/0128252 | A1 | 9/2002 | Glombik | JP | 121479 | 12/1986 |
| 2002/0128253 | A1 | 9/2002 | Glombik | JP | 219681 | 4/1987 |
| 2002/0132855 | A1 | 9/2002 | Nelson | JP | 61280295 A | 12/1987 |
| 2002/0137689 | A1 | 9/2002 | Glombik | JP | 63017859 A | 1/1988 |
| 2002/0147184 | A1 | 10/2002 | Kosoglou et al. | JP | 91068020 | 10/1991 |
| 2002/0151536 | A1 | 10/2002 | Davis | JP | 4054182 A | 2/1992 |
| 2002/0169134 | A1 | 11/2002 | Davis | JP | 4266869 A | 9/1992 |
| 2002/0183305 | A1 | 12/2002 | Davis et al. | JP | 4356495 | 12/1992 |
| 2002/0192203 | A1 | 12/2002 | Cho et al. | | | |

| | | | | | | |
|---|---|---|---|---|---|---|
| JP | 5194209 A | 8/1993 | | WO | WO 99/66930 | 12/1999 |
| JP | 5239020 A | 9/1993 | | WO | WO 00/04011 | 1/2000 |
| JP | 5058993 A | 10/1993 | | WO | WO 00/07617 | 2/2000 |
| JP | 4356195 A | 12/1993 | | WO | WO 00/16749 | 3/2000 |
| JP | 94047573 | 6/1994 | | WO | WO 00/18395 | 4/2000 |
| JP | 95051558 B2 | 6/1995 | | WO | WO 00/20623 | 4/2000 |
| WO | WO 82/01649 | 5/1982 | | WO | WO 00/23415 | 4/2000 |
| WO | WO 87/04429 | 7/1987 | | WO | WO 00/23416 | 4/2000 |
| WO | WO 88/04656 | 6/1988 | | WO | WO 00/23425 | 4/2000 |
| WO | WO 88/05296 | 7/1988 | | WO | WO 00/23445 | 4/2000 |
| WO | WO 91/03249 | 3/1991 | | WO | WO 00/23451 | 4/2000 |
| WO | WO 92/13837 | 8/1992 | | WO | WO 00/28981 | 5/2000 |
| WO | WO 93/02048 | 2/1993 | | WO | WO 00/31548 | 6/2000 |
| WO | WO 93/07167 | 4/1993 | | WO | WO 00/32189 | 6/2000 |
| WO | WO 93/11150 | 6/1993 | | WO | WO 00/34240 | 6/2000 |
| WO | WO 94/00480 | 1/1994 | | WO | WO 00/37057 | 6/2000 |
| WO | WO 94/14433 | 7/1994 | | WO | WO 00/37078 | 6/2000 |
| WO | WO 94/17038 | 8/1994 | | WO | WO 00/38721 | 7/2000 |
| WO | WO 94/20535 | 9/1994 | | WO | WO 00/38722 | 7/2000 |
| WO | WO 94/26738 | 11/1994 | | WO | WO 00/38723 | 7/2000 |
| WO | WO 95/04533 | 2/1995 | | WO | WO 00/38724 | 7/2000 |
| WO | WO 95/06470 | 3/1995 | | WO | WO 00/38725 | 7/2000 |
| WO | WO 95/08532 | 3/1995 | | WO | WO 00/38726 | 7/2000 |
| WO | WO 95/18143 | 7/1995 | | WO | WO 00/38727 | 7/2000 |
| WO | WO 95/26334 | 10/1995 | | WO | WO 00/38728 | 7/2000 |
| WO | WO 95/28919 | 11/1995 | | WO | WO 00/38729 | 7/2000 |
| WO | WO 95/35277 | 12/1995 | | WO | WO 00/40247 | 7/2000 |
| WO | WO 96/00288 | 1/1996 | | WO | WO 00/45817 | 8/2000 |
| WO | WO 96/09827 | 4/1996 | | WO | WO 00/50392 | 8/2000 |
| WO | WO 96/16037 | 5/1996 | | WO | WO 00/53149 | 9/2000 |
| WO | WO96/19450 | 6/1996 | | WO | WO 00/53173 | 9/2000 |
| WO | WO 96/19987 | 7/1996 | | WO | WO 00/53563 | 9/2000 |
| WO | WO 96/40255 | 12/1996 | | WO | WO 00/56403 | 9/2000 |
| WO | WO 97/16455 | 5/1997 | | WO | WO 00/57859 | 10/2000 |
| WO | WO 97/18304 | 5/1997 | | WO | WO 00/57918 | 10/2000 |
| WO | WO 97/21676 | 6/1997 | | WO | WO 00/60107 | 10/2000 |
| WO | WO 97/25042 | 7/1997 | | WO | WO 00/63153 | 10/2000 |
| WO | WO 97/28149 | 8/1997 | | WO | WO 00/63161 | 10/2000 |
| WO | WO 97/31907 | 9/1997 | | WO | WO 00/63190 | 10/2000 |
| WO | WO 97/35576 | 10/1997 | | WO | WO 00/63196 | 10/2000 |
| WO | WO 97/41098 | 11/1997 | | WO | WO 00/63209 | 10/2000 |
| WO | WO 97/46238 | 12/1997 | | WO | WO 00/63703 | 10/2000 |
| WO | WO 98/01100 | 1/1998 | | WO | WO 00/69412 | 11/2000 |
| WO | WO 98/05331 | 2/1998 | | WO | WO 00/69445 | 11/2000 |
| WO | WO 98/14179 | 4/1998 | | WO | WO 00/72825 | 12/2000 |
| WO | WO 98/31360 | 7/1998 | | WO | WO 00/72829 | 12/2000 |
| WO | WO 98/31361 | 7/1998 | | WO | WO 00/75103 | 12/2000 |
| WO | WO 98/31366 | 7/1998 | | WO | WO 00/76482 | 12/2000 |
| WO | WO 98/43081 | 10/1998 | | WO | WO 00/76488 | 12/2000 |
| WO | WO 98/46215 | 10/1998 | | WO | WO 00/78312 | 12/2000 |
| WO | WO 98/47518 | 10/1998 | | WO | WO 00/78313 | 12/2000 |
| WO | WO 98/57652 | 12/1998 | | WO | WO 01/00579 | 1/2001 |
| WO | WO 99/06035 | 2/1999 | | WO | WO 01/00603 | 1/2001 |
| WO | WO 99/06046 | 2/1999 | | WO | WO 01/08686 | 2/2001 |
| WO | WO 99/08501 | 2/1999 | | WO | WO 01/12176 | 2/2001 |
| WO | WO 99/09967 | 3/1999 | | WO | WO 01/12187 | 2/2001 |
| WO | WO 99/11260 | 3/1999 | | WO | WO 01/12612 | 2/2001 |
| WO | WO 99/12534 | 3/1999 | | WO | WO 01/14349 | 3/2001 |
| WO | WO 99/04815 | 4/1999 | | WO | WO 01/14350 | 3/2001 |
| WO | WO 99/15159 | 4/1999 | | WO | WO 01/14351 | 3/2001 |
| WO | WO 99/15520 | 4/1999 | | WO | WO 01/15744 | 3/2001 |
| WO | WO 99/18072 | 4/1999 | | WO | WO 01/16120 | 3/2001 |
| WO | WO 99/20275 | 4/1999 | | WO | WO 01/17994 | 3/2001 |
| WO | WO 99/20614 | 4/1999 | | WO | WO 01/18210 | 3/2001 |
| WO | WO 99/22728 A1 | 5/1999 | | WO | WO 01/21181 | 3/2001 |
| WO | WO 99/29300 | 6/1999 | | WO | WO 01/21259 | 3/2001 |
| WO | WO 99/38498 | 8/1999 | | WO | WO 01/21578 | 3/2001 |
| WO | WO 99/38845 | 8/1999 | | WO | WO 01/21647 | 3/2001 |
| WO | WO 99/38850 | 8/1999 | | WO | WO 01/22962 | 4/2001 |
| WO | WO 99/46232 | 9/1999 | | WO | WO 01/25225 | 4/2001 |
| WO | WO 99/47123 | 9/1999 | | WO | WO 01/25226 | 4/2001 |
| WO | WO 99/48488 | 9/1999 | | WO | WO 01/30343 | 5/2001 |
| WO | WO 99/66929 | 12/1999 | | WO | WO 01/32161 | 5/2001 |

| | | |
|---|---|---|
| WO | WO 01/34148 | 5/2001 |
| WO | WO 01/35970 | 5/2001 |
| WO | WO 01/40192 | 6/2001 |
| WO | WO 01/45676 | 6/2001 |
| WO | WO 01/49267 | 7/2001 |
| WO | WO 01/60807 | 8/2001 |
| WO | WO 01/64221 | 9/2001 |
| WO | WO 01/76632 | 10/2001 |
| WO | WO 01/96347 A1 | 12/2001 |
| WO | WO 02/08188 | 1/2002 |
| WO | WO 02/26729 | 4/2002 |
| WO | WO 02/50027 | 6/2002 |
| WO | WO 02/50060 | 6/2002 |
| WO | WO 02/50068 | 6/2002 |
| WO | WO 02/50090 | 6/2002 |
| WO | WO 02/058685 | 8/2002 |
| WO | WO 02/058696 | 8/2002 |
| WO | WO 02/058731 | 8/2002 |
| WO | WO 02/058732 | 8/2002 |
| WO | WO 02/058733 | 8/2002 |
| WO | WO 02/058734 | 8/2002 |
| WO | WO 02/058734 A | 8/2002 |
| WO | WO 02/064094 | 8/2002 |
| WO | WO 02/064130 | 8/2002 |
| WO | WO 02/064549 | 8/2002 |
| WO | WO 02/064664 | 8/2002 |
| WO | 02/070523 A1 | 9/2002 |
| WO | WO 02/070523 A | 9/2002 |
| WO | WO 02/072104 | 9/2002 |
| WO | WO 02/081454 | 10/2002 |
| WO | WO 03/018024 | 3/2003 |
| WO | WO 03/018059 | 3/2003 |
| WO | WO 03/039542 | 5/2003 |
| WO | WO 03/074101 | 9/2003 |
| WO | WO 03/082192 A | 10/2003 |
| WO | WO 03/088962 | 10/2003 |

OTHER PUBLICATIONS

*Exhibit A*: SCH 58235 Micronized (ezetimibe), Drug Formulation Development Summary.
*Exhibit B*: SCH 58235 (ezetimibe), Drug Formulation Development Summary.
*Exhibit C*: SCH 58235 (ezetimibe), Drug Formulation Development Summary.
*Exhibit D*: SCH 58235 (ezetimibe), Drug Formulation Development Summary.
*Exhibit E*: SCH 58235 (ezetimibe), Drug Formulation Development Summary.
*Exhibit F*: SCH 58235 (ezetimibe), Drug Formulation Development Summary.
*Exhibit G*: SCH 58235 (ezetimibe), Drug Formulation Development Summary.
*Exhibit H*: SCH 58235 (ezetimibe), Drug Formulation Development Summary.
*Exhibit 1*: Master Sheet for the SCH 58235 and Lovastatin Research Study, *Schering-Plough Research Institute* (Protocol No. C906-411), p. 1576-1585.
*Exhibit 2*: Medical Research Study #1055/97, SCH 58235: Bioavailability of Single Oral Doses of Two Prototype Tablet Formulations and the Reference Capsule Formulation of SCH 58235 in Normal Male Volunteers: A Four Way Crossover Study #C97-221-01, Informed Consent, *Peninsular Testing Corporation*, p. 106-112.
*Exhibit 3*: Consent Form to Participate in a Research Study, "A Phase II Double Blind Dose Response Investigation of Efficacy and Safety of Four Doses of SCH 58235 Compared to Placebo in Subjects with Primary Hypercholesterolemia," *Schering-Plough Research Institute* (Protocol No. C98-010), p. 1558-1566.
*Exhibit 4*: Medical Research Study #1096/99, SCH 58235: Pharmacokinetic Pharmacodynamic Drug Interaction Study with Digoxin in Healthy Volunteers #C98-114, Informed Consent, *Peninsular Testing Corporation*, p. 124-130.

*Exhibit 5*: Informed Consent, "SCH 58235: Assessment of Multiple-Dose Drug Interaction Between 58235 and Gemfibrozil in Healthy Volunteers," *Schering-Plough Research Institute*, p. 1-8.
Vaccaro, W.D. et al , "Sugar-substituted 2-azetidinone cholesterol absorption inhibitors: enhanced potency by modification of the sugar" *Bioorganic & Medicinal Chemistry Ltrs.*, Oxford, G.B., 8:313-318 (1998).
Vaccaro, W.D. et. al., "Carboxy-substituted 2-azetidinones as cholesterol absorption inhibitors", *Bioganic & Medicinal Chem. Ltrs.* Oxford, G.B. 8:319-322 (1998).
H. Davis et al., "Ezetimibe, a Potent Cholesterol Absorption Inhibitor, Inhibits the Developmentof Aterosclerosis in Apo E Knockout Mice", *Arterioscler, Thromb. Vasc. Biol* 21:2032-2038, (Dec. 2001).
Simova, E., "Aldol-type addition of hydrocinnamic acid esters to benzylideneaniline", *Chemical Abstracts* No. 15, 86 (Apr. 11, 1997).
Otto et al., Stereochemistry of dehydration and halogenation fo $\alpha R^*$ and $\alpha S^*$ isomeric 3-($\alpha$-hydroxybenzyl)-1,4 diphenyl=2 azetidinones, *Chemical Abstracts* No. 19, 99 (Nov. 7, 1983).
T. Durset et al., "Metallation of N-Substituted $\beta$-Lactams. A Method of the Introduction of 3-substituents into $\beta$-Lactams" *Canadian Journal of Chemistry*, 50:3196-3201 (1971).
Nobuki, O. et al., "Stereoselective syntheses of b-lactam derivatives by ultrasound promoted Reformatskii reaction" *Chemical Abstracts* No. 106, 17 (Apr. 27, 1987).
M. Hoekman, et al., "Synthesis of Homologues of 4,5-Dihydroxy- and 4-Hydroxy-5-oxohexanoic Acid $\gamma$-Lactones", *J. Agric. Food Chem.*, 30:920-024 (1982).
H. Otto et al. "Darstellung and Stereochemie von 3-($\alpha$-Hydroxybenzyl)-1,4-diphenyl-2-azetidononen", *Liebigs Ann. Chem.* 1152-1161 (1983).
G. George et al. "3-(1'-Hydroxyethyl)-2-Azetidinones From 3-Hydroxybutyrates and N-Arylaldimines" *Tetrahedron Letters*, 26:3903-3906 (1985).
Hart et al. "An Enantioselective Approach to Carbapenem Antibodies: Formal Synthesis of (+)-Thienamycin", 26 *Tetrahedron Letters*, 45:5493-5496 (1985).
Penfil, I. et al. "Synthesis of $\beta$-Lactams from $\alpha$, $\beta$-Unsaturated Sugar $\delta$-Lactones" 24 *Heterocycles* 6:1609-1617 (1986).
D. Roger Illingworth, "An Overview of Lipid-Lower Drugs" *Drugs* 36:63:71 (1988).
Joseph L. Witztum, M.D., "Current Approaches to Drug Therapy for the Hyercholesterolemic Patient" *Circulation* 80:1101-1114 (1989).
B. Ram et al. "Potential Hypolipidemic agents:Part V", 29B Indian J. Chem. 1134-37 (1990).
Schnitzer-Polokoff, R. et al., "Effects of Acyl-CoA: Choleseraol O-Acyltransferase Inhibition on Cholesterol Absorption and Plasma Lipoprotein Composition in Hamsters" Comp. Biochem. Physiol. 99A:665-670 (1991).
Horie, M. et al, "Hypolipodemic effects of NB-598 in dogs" *Atherosclerosis* 88:183-192 (1991).
Baxter, A., "Squalestatin 1, a Potent Inhibitor of Squalene Synthase, Which Lowers Serum Cholesterol in Vivo", *The Journal of Biological Chemistry* 267:11705-11708 (1992).
Summary Factfile, "Anti-Atherosclerotic Agents" *Current Drugs Ltd.* (1992).
Harwood H. James, "Pharmacologic consequences of cholesterol absorption inhibition: alteration in cholesterol metabolism and reduction in plasma cholesterol concentration induced by the synthetic saponin $\beta$-tigogenin cellobioside (CP-88818; tiqueside) 1" *Journal of Lipid Research* 34:377-395 (1993).
Salisbury, B. et al., "Hypocholesterolemic activity of a novel inhibitor of cholesterol absorption, SCH 48461" *Atherosclerosis* 115:45-63 (1995).
Clader, J.W. et al., "Substituted (1,2-Diarylethyl)amide Acyl-CoA;Cholesterol Acyltransferase Inhibitors: Effect of Polar Groups in Vitro and in Viro Activity" *Journal of Medicinal Chemistry* 38:1600-1607 (1995).
Sybertz, E., "Sch 48461, a novel inhibitor of cholesterol absorption" Atherosclerosis pp. 311-315 (1995).
Vaccaro, W, et al, "2-Azetidinone Cholesterol Absorption Inhibitors; Increased Potency by Substitution of the C-4 Phenyl Ring", *Bioorg. & Med. Chem.* 6:1429-1437 (1998).

G. Wu et al, A Novel One-Step Diastereo-and enantioselective formation of trans-azetidinones and its application to the total synthesis of cholesterol absorption inhibitors A.C.S. (Apr. 21, 1999).

B. Staels, "New Roles for PPARS in Cholesterol Homeostasis", *Trends in Pharmacological Sciences*, 22:9 p. 444 (Sep. 2001).

Abbott et al, "Tricor® Capsules, Micronized", *Physicians Desk Reference*, Jan. 8, 2001.

M. Feher et al., 1991, Lipids and Lipid Disorders, p. 1-87 (1991).

M. Ricote et al., "New Roles for PPARs in Cholesterol Homeostakis", *Trends in Pharmacological Science*, vol. 22, No. 9 44-443 (2001).

C. Dujovne et al, "Reduction of LDL Cholesteral in Patients with Primary Hypercholesterolemia by SCH 48461: Results of a multicenter Dose-Ranging Study", *J. Clin,. Pharm*. 41:1 70-78 (Jan. 2001).

W. Oppolzer et al., "Asymmetric Diels—Alder Reactions, Facile Preparation and Structure of Sulfonamido—Isobornyl Acrylates", *Tetrahedron Letters* No. 51, 25:5885-5888 (1984).

M. Davidson et al., "Colesevelam Hydischloride: a non-absorbed, polymeric cholesterol lowering agent", *Expert Opinion Investigating Drugs*, 11:2663-71, (Nov. 2000).

M. Davidson et al., "Colesevelam hydrochloride (cholestagel): a new, potent bileacid sequestrant associated with a low incidence of gastrointestinal effects", 159 *Arch. Intern. Med*. 16 1893-900 (Sep. 1999).

I. Wester, "Cholesterol—Lowering effect of plant sterols", *Euro. J.Lipid, Sci. Tech*. 37-44 (2000).

A. Andersson et al., "Cholesterol -lowering effects of a stanol ester-containing low fat margarine used in conjunction with a strict lipid-lowing diet", *1 European Heart J. Supplements* S80-S90 (1999).

H. Gylling et al, Reduction of Serum Cholesterol in Postmenopausal Women with Previous Myocardial Infarction and Cholesterol Malabsorption induced by Dietary Sitostarol Ester Margarine, *96 Circulation12* 4226-4231 (Dec. 16, 1997).

T. Miettinen et al. "Reduction of Serum Cholesterol with Sitostanol-Ester Margarine in a Mildly Hypercholesterolemic Population", *New England Journal of Med*. 333 1308-1312 (Nov. 16, 1995).

T. Bocan et al., "The ACAT Inhibitor Avasimibe Reduces Macrophages and Matrix Metalloproteinase Expression in Atherosclerotic Lesions of Hypercholesterolemic Rabbits", *Arterioscler Thromb Vasc. Biol*. 70-79 (Jan. 2000).

M. Van Heek et al., "In Vivo Metabolism—Based Discovery of a Potent Cholesterol Absorption Inhibitor, SCH 58235, in the Rat and Rhesus Monkey through the indentification of the active metabolites of SCH48461," *283 J. Pharma and Experimental Therapeutics* 1 157-163 (1997).

H. Davis et al., "The Cholesterol Absorption Inhibitor Ezetimible Inhibits the Development of Atherosclerosis in apo E knockout (−/−) mice fed low fat and western diets," *151 Atherosclerosis* 1:133 (Jul. 2000).

L. Nguyen et al., "Unexpected Failure of Bile Acid Malabsorption to Stimulate Cholesterol Synthesis in Sitosterolemia with Xanthomatosis", *10 Atherosclerosis* 2, 289-297 (1990).

L. Nguyen et al., "Regulation of Cholesterol Biosynthesisin Sitosterolemia: effects of lovastatin, Cholestyramine, and dietary sterol restriction," *32 J.Lipid Res*. 1941-1948 (1991).

M. Cobb et al., "Sitosterolemia: Opposing Effects of cholestyramine and Lovastatin on Plasma Sterol Levels in a Homozygous Girl and Her Heterozygous Father," *45 Metabolism* 6 673-679 (Jun. 1996).

M. Huettinger et al., "Hypolipidemic Activity of HOE-402 is mediated by Stimulation of the LDL Receptor Pathway", *13 Arteriosclerosis and Thrombosis* 7 1005-1012 (Jul. 1993).

J. Best et al., "Diabetic Dyslipidaemia", *59 Drugs* 5 1101-1111 (May 2000).

P. Chong, et al, "Current, New and Future Treatment in Dyslipidaemia and Atherosclerosis", *60 Drugs* 1 55-93 (Jul. 2000).

M. Brown et al, "A Receptor—Mediated Pathwawy for Cholesterol Homeostasis", *232 Science* 34-47 (Apr. 4, 1986).

L. Lipka et al., "Reduction of LDL-Cholesterol and Elevation of HDL-Cholesterol in Subjects with Primary Hypercholesterolemia by SCH 58235: Pooled Analysis of Two Phase II Studies", *JACC* 257A (Feb. 2000).

Medical Economics, Co., Inc., *Physician's Desk Reference*, 207-208, 2054 (55$^{th}$ Ed. 2001).

K. Fassbender et al., "Simvastatin Strongly Reduces Levels of Alzheimer's Disease β-Amyloid Peptides Aβ 42 and Aβ40 in vitro and in vivo", *PNAs Early Edition*, www.phas.org/cgi/doi/10,1073/phas.081620098 (2001).

Andrx Announces Results of Alzheimer's Disease Clinical Study, *Andrx Corporate Release* (Apr. 11, 2001).

Andrx (ADRX): Pos Phase II Results Using Avicor in Alzheimer's: Str Buy; $130,*US Bancorp Piper*, Apr. 12, 2001.

Statins May Protect Against Alzheimer's Disease; much research needed, *Geriatrics* Feb. 2001.

Dementia and Statins, *The Lancet* Mar. 17, 2001.

Research & Development: Andrx Says Cholesterol Drug May Treat Alzheimers, *Reuters* Apr. 11, 2001.

Cholesterol Drugs Ease Alzheimer's Damage; www.usatoday.com Apr. 10, 2001.

Lovastation XL of Use in Alzheimer's? News Edge (May 2, 2001).

L. Refolo et al, Hypercholesterolemia Accelerates the Alzheimer's Amyloid Pathology in a Transgenic Morse Model, *Neurobiology of Disease* 321-331 (2000).

D. Kang et al., "Modulation of Amyloid β-protein Clearance and Alheimer's Disease Susceptibility by the LDL Receptor—Relatead Protein Pathway", *Journal of Clinical Investigation* 106:9, 1159-1166 (Nov. 2000).

Y.A. Kesaniewmi, "Intestinal Cholesterol Absorption Efficiency in Man in Related to Apoprotein E Phenotype", *J. Clin. Invest*. 80(2) 578-81 (Aug. 1987).

J. Busciglio et al., "Generation of β-amyloid in the secretary pathway in neuronal and nonneuronal cells", *90 Proc. Nat'l. Acad. Sci, USA*, 2092-2096 *Neurobiology* (Mar. 1993).

L. Farrer et al., "Assessment of Genetic Risk for Alzheimer's Disease Among first Degree Relatives", *Annals of Neurobiology* 25:5, 485-493 (May 1989).

A. Goate et al., "Segregation of a Missense Mutation in the Amyloid Precursor Protein Gene with Familial Alzheimer's Disease", *349 Nature* No. 6311, 704-706 (Feb. 21, 1991).

D. Mann et al., "The Pattern of Acquisition of Plaques and Tangle in the Brains of Patients Under 50 years of Age with Down's Syndrome", *89 J. Neuro. Sci*., 169-179 (Feb. 1989).

G. McKhann et al., "Clinical Diagnosis of Alzheimer's Disease", *34 Neurology* No. 7, 939-944 (Jul. 1984).

D. Selokoe, "Alzheimer's Disease: Genotypes, Phenotype and Treatments", *275 Science*, 630-631 (Jan. 31, 1997).

C. Van Duijn, et al., "Familial Aggregation of Alzheimer's Disease and Related Disorders: A collaborative Re-Analysis of Case-Control Studies", *20 Int'l J. Epidemiology* No. 2, (*Suppl. 2*), 513-520 (1991).

T Nagahara et al., "Dibasic (Amidcinoaryl) Propanoic Acid Derivatives as Novel Blood Coagulation Factor Xa Inhibitors", J. Med. Chem 37:1200-1207 (1994).

Mellott et al., "Acceleration of Recombinant Tissue-Type Plasminogen Activator Induced Reperfusion and Prevention of Reocculsion by Recombinant Antistasin, a selective factor Xa Inhibitor, in a Canine Model of Femoral Arterial Thrombosis", *Circulation Research*, 70:1152-1160 (1992).

Sitko et al., "Conjunctive Enhancement of Enzymatic Thrombolysis and Prevention of Thrombotic Reocclusion With the Selective Factor Xa Inhibitor, Tick Anticoagulant Peptide", *Circulation*, 85:808-815 (1992).

Seymour et al., 1994, *Biochemistry*, 33:3949-3959.

Markwardt, 1994, *Thrombosis and Hemostasis*, 72:477-479.

Mendall et al., "C-Reactive Protein and its relation to cardiovascular risk factor: A population based cross sectional study", *BMJ*; 312:1061-1065 (Apr. 27, 1996).

Ridker P. et al., "Prospective Studies of C-Reactive Protein as a risk factor for cardiovascular disease", 46 *J. Investig. Med.*; 8:391-395 (1998).

Waters, D. et al., "A Controlled Clinical Trial to Assess the Effect of a Calcium Channel Blocker on the Progression of Coronary Atherosclerosis", *Circulation*; 82:1940-1953 (1990).

Fleckenstein, 1985, *Cir. Res*. vol. 52 (Suppl. 1) 13-16.

Fleckenstein, 1983, "Experimental Facts ad Therapeutic Prospects", *John Wiley*, New York, pp. 286-313.

McCall, D., 1985, *Curr. Pract. Cardiol.* vol. 10, 1-11.

Remington 1995, The Science and Practice of Pharmacy, (19th Ed. 1995) p. 963.

M. Chistie et al., "Early—Onset Amyloid Deposition and Cognitive Deficits in Transgenic Mice Expressing a Double Mutant Form of Amyloid Precursor Protein 695", 276 *J. Biol. Chem.* No. 24; 21562-70 (Jun. 15, 2001).

C. Janus et al., "Aβ Peptide Immunization Reduces Behavioral impairment and Plaques in a Model of Alzheimer's Disease", *408 Nature* 21/28; 979-982 (Dec. 2000).

Manual of Laboratory Operations, Lipid Research Clinics Program Report, Washington, D.C., *U.S. Dept. of Health, Education and Welfare Publication*; 1:75-628 (1974).

Steiner, PM et al., Standardization of Micromethods for Plasma Cholesterol, Triglyceride and HDL-Cholesterol with the Lipid Clinic's Methodology [abstract], *J. Clin. Chem. Clin. Bichem*; 19:850 (1981).

Steele WG, et al., Enzymatic Determinations of Cholesterol in High Density Lipoprotein Fractions Prepared by Precipitation Technique,22 *Clin. Chem.*; 1:98-101 (1976).

Salen et al., "Increased Sitosterol Absorption, Decreased Removal and Expanded Body Pools Compensate for Reduced Choelsterol Syntheses in Sitosterolemia with Xanthomatosis", *J. Lipd Res..*; 30:1319-1330 (1989).

Lutjohann et al., "Sterol Absorption and Sterol Balance in Phytosterolemia Evaluated by Deuterium-Labeled Sterols: Effect of Sitostanol Treatment", *J. Lipid Res.*; 36:8; 1763-1773 (1995).

Zhang et al., "Calpain Inhibitor I Increases B- Amyloid Peptide by Inhibiting the Degradation of the Substrate of γ- Secretase" 274 *J. Biol, Chem.*, 13:8966-8972 (1999).

Zhang et al., "Biochemical Characterization of the γ-Secretase Activity that Produces B-Amyloid Peptides", Biochemistry 40:5049-5055 (2001).

Ida et al., "Analysis of Heterogeneous BA4 Peptides in Human Cerebrospinal Fluid and Blood by a Newly Developed Sensitive Wertern Blot Assay", 271 *J. Biol, Chem.*; 37:22908-22914 (1996).

Lichtlen, P.R. et al., 1990, *Lancet*; 335:1109-1113.

Bays et al., "Effectiveness and Tolerability of Ezetimibe in Patients with Primary Hypercholesterolemia: Pooled Analysis of Two Phase II Studies", *Clinical Therapeutics*, 23:1209-1230 (2001).

E. Leitersdorf et al., "Cholesterol absorption inhibition: filling an unmet need in lipid-lowering management", *European Heart Journal Supplimrnt*, 3:E17-E23 (Jun. 2001).

Bauer et al., "Ezetimibe Does not Affect the Pharmacokinetics or Pharmacodynamics of Warfarin", *Clinical Pharmacology and Therapeutics*, 69:2 p. 5 (Mar. 6-10, 2001).

Keung et al., Ezetimibe Does Not Affect the Pharmacokinetics of oral Contraceptives, *Clinical Pharmacology and Therapeutics*, 69:2 p. 55 (Mar. 6-10, 2001).

Kosoglou et al., "Pharmacodynamic interaction between fenofibrate and the Cholesterol Absorption Inhibitor Ezetimibe", *Workshops Lipid Lowering Drugs 72nd EAS Congress*, p. 38 (May 21-23, 2001).

T. Kosoglou et al., "Coadministration of Ezetimibe and Fenofibrate Leads to Favorable Effects On Apo CII and LDL Subfractions", *Posters 11. Lipid Lowering Drugs/Novel, 72nd EAS Congress*, p. 89 (May 21-23, 2001).

L. Reyderman et al., "Assessment of a Multiple-Dose Drug Interaction Between Ezetimibe and Gemfibrozil", Presented at XIV Int'l Symp. on Drugs Affecting Lipid Metabolism (DALM) N.Y. (Sep. 9-12, 2001).

P. Statkevich et al., "Ezetimibe Does Not Affect the Pharmacokinetics and Pharmacodynamics of Glipizide", *Clinical Pharmacology & Therapeutics*, 69:67 (Mar. 6-10, 2001).

Knopp et al, "Effect of Ezetimibe on Serum Concentrations of Lipid-Soluble Vitamins", *Posters 11. Lipid Lowering Drug/Novel 72nd EAS Congress*, p. 90 (May 21-23, 2001).

Kosoglou et al., "Pharmacodynamic Interaction Between Fenofibrate and the Cholesterol Absorption Inhibitor Ezetimibe", *Workshops Lipid Lowering Drugs, 72nd EAS Congress*, p. 38 (Mar. 6-10, 2001).

Bays et al., "Low-Density Lipoprotein Cholesterol Reduction By SCH 58235 (Ezetimibe), A Novel Inhibitor of Intestinal Cholesterol Absorption, in 243 Hypercholesterolemic Subjects: Results of a Dose-Response Study", *XII International Symposium on Atherosclerosis*, Stockholm, Sweden (Jun. 25-29, 2000).

Castaner et al, "Ezetimibe—Hypolipidemic Cholesterol Absorption Inhibitor", *Drugs of the Future*, 25(7):679-685 (2000).

Lipka et al., "Reduction of LDL-Cholesterol and Elevation of HDL-Cholesterol in Subjects with Primary Hypercholesterolemia by Ezetimibe (SCH 58235): Pooled Analysis of Two Phase II Studies", *American College of Cardiology Annual Meeting*, Anaheim, CA (Mar. 12-15, 2000).

Van Heek et al., "Comparison of the activity and disposition of a novel cholesterol absorption inhibitor , SCH58235, and its glucuronide, SCH60663", *British Journal of Pharmacology*, 129:1748-1754 (2000).

Van Heek et al., 2000, "The potent cholesterol absorption inhibitor, ezetimibe, is glucuronidated in the intestine, localizes to the intestina, and circulates enterohepatically", *XII International Symposium of Atherosclerosis*, Stockholm Sweden (Jun. 25-29, 2000).

Iannucci et al., "Metabolism of SCH 58235 in the Human, Rat and Dog", *47th ASMS Conference on Mass Spectrometry and Allied Topics*, Dallas, TX (Jun. 13-17, 1999).

Reiss et al., "An Enzymatic Synthesis of Glucuronides of Azetidinone-based Cholesterol Absorption Inhibitors", *Bioorganic & Medicinal Chemistry*, 7:2199-2202 (1999).

Rosenblum et al., "Discovery of 1-(4-Flurophenyl)-(3R)-[3-(4-fluorophenyl)-(3S)-hydroxypropyl]-(4S)-(4-hydroxyphenyl)-2-azetidinone (SCH 58235): A Designed, Potent, Orally Active Inhibitor of Cholesterol Absorption", *J. Med. Chem.* 41:973-980 (1998).

Vaccaro et al., "Sugar-Substituted 2-Azetidinone Cholesterol Absorption Inhibitors: Enhanced Potency by Modification of the Sugar", *Bioorganic & Medicinal Chemistry Letters*, 8:313-318 (1998).

Zaks et al., "Enzymatic Glucuronidation of a Novel Cholesterol Absorption Inhibitor, SCH 58235", *Applied Biochemistry and Biotechnology*, 73:205-214 (1998).

W. Insull et al., Postmenopausal Hypercholesterolemic Women Derive Additive Benefit from Raloxifene and Simvastatin on Lipid Parameters , *World Heart Federation 6th International Symposium on Global Risk of Coronary Heart Disease and Stroke—Abstract Book*, p. 35 (Jun. 12-15, 2002).

L. Simons et al., 2002, "Ezetimibe added to on-going statin therapy for treatment of primary hypercholesterolemia: Efficacy and safety in patients with Type 2 diabetes mellitus", presented at the 38th Annual Meeting of the EASD, Sep. 1-5, 2002.

C. Allain et al, 1974, "Enzymatic Determination of Total Serum Cholesterol", *Clinical Chemical*, 20:470-475.

R. Mayrhofer et al., 1980, "Simple-Preparation of 3-Benzylidene-2-azetilidinones", *Synthesis*, 247-248.

Burrier, R.E. et al., 1994, "Demonstration of a Direct Effect of Hepatic Acyl CoA:Cholesterol Acyl Transferase (ACAT) Activity By An Orally Administered Enzyme Inhibitor in the Hamster", *Biochemical Pharmacology* 47:15451551.

Burrier, R.E. et al., 1994, "The Effect of Acyl CoACholesterol Acyltransferase Inhibitor on the Uptake, Esterification and Secretion of Cholesterol by the Hamster Small Intestine", *The Journal of Pharmacology and Experimental Therapeutics* 272:156-163.

E.F. Binder et al., "Effects of Hormone Replacement Therapy on Serum Lipids in Elderly Women. A Randomized, Placebo-Controlled Trial", *134 Ann. Intern. Med.* 9:754-760 (May 1, 2001).

MR Haymart et al., "Optimal Management of Dyslipidemia in Women and Men", 2 *J. Gend. Specif. Med.* 6:37-42 (Nov.-Dec. 1997).

"Framingham Heart Study Analysis Reveals Some Primary Prevention Subgroups Are Being Overlooked", *Heartwire* (Apr. 12, 2001).

"Detection Evaluation, and Treatment of High Blood Cholesterol in Adults (Adult Treatment Panel III), Third Report of the National Cholesterol Education Program (NCEP)", *NIH Publication* No. 01-3670 (May 2001).

Van Heek et al., "Ezetimibe, A Potent Cholesterol Absorption Inhibitor, Normalizes Combined Dyslipidemia in Obese Hyperinsulinemic Hamsters", 50 *Diabetes* 1330-1335 (Jun. 2001).

"Additional Statins Show Anti-Inflammatory Effect", 103 *Circulation* 1933-35 (Apr. 17, 2001).

H. Hauser, et al, "Identification of a Receptor Mediating Absorption of Dietary Cholesterol in the Intestine", *Biochemistry* 37:17843-17850, 1998.

G. Salen, et al., "Sitosterolemia", *Journal of Lipid Research* 33:945-955, 1992.

Stedman's Medical Dictionary, 27th Edition, p. 1381.

Stuart B. Rosenblum et al., Discovery of 1-(4-Fluorophenyl)-(3R)-[3-(fluorophenyl)-(3S)-hydroxypropyl]-(4S)-(4-hydroxyphenyl)-2-azetidinone (SCH 58235): A Designed, Potent, Orally Active Inhibitor of Cholesterol Absorption, *J. Med. Chem.* 41:973-980 (1998).

Remington's Pharmaceutical Sciences, 18th ed. 1990 p. 1319, 1633-1647.

Baker S G et al., Treatment of homozygous familial hypercholesterolaemia with probucol, *South African Medical Journal* (1982).

R. Milanese et al., Xantomi E Ipercolesterolemia: Prevalenza, Diagnosi e Terapia, *Chron. Derm.* 455-61 (1990).

"Study showed ezetimibe significantly reduced levels of LDL cholesterol or "bad" cholesterol in patients" *Schering Press Release* 1-3 (2001).

Kosoglou et al., "Pharmacodynamic interaction between fenofibrate and the cholesterol absorption inhibitor ezetimibe" *Atherosclerosis* (2):3(2001).

Davis et al., "The Synergistic Hypocholesterolemic Activity of the Potent Cholesterol Absorption Inhibitor, Ezetimibe, in Combination with 3-Hydroxy-3-Methylglutaryl Coenzyme A Reductase Inhibitors in Dogs" *Metabolism* 50(10):1234-1241(2001).

Thompson, G.R. et al., "Novel lipid-regulating drugs" *Expert Opinion on Investigational Drugs* 9(11):2619-2628 (2000), XP008011782 abstract; figure 8.

Kosoglou, T. et al., "Coadministration of ezetimibe and fenofibrate leads to favorable effects on Apo CII and LDL subfractions" *Atherosclerosis* 2:89 (2001), XP001132089 abstract.

Gilber R. Thompson et al., Novel lipid-regulating drugs, Ashley Publications Ltd. ISSN 1354-3784, 2000, pp. 2619-2628.

Belamarich P.F. et al., Response to diet and cholestyramine in a patient with sitosterolemia, Pediatrics, ISSN 0031-4005, Dec. 1990.

Salen G. et al., Lethal atherosclerosis associated with abnormal plasma and tissue sterol composition in sitosterolemia with xanthomatosis, Journal of lipid research, ISSN 0022-2275, Sep. 1985.

Sorbera et al., Netoglitazone, *Drugs of the Future*, 2002, 27(2): 132-139.

Michel Farnier, Nouvelles approaches médicamenteuses dans le traitement des dyslipidémies, *MT Endocrinologie*, 2002, 4:252-259.

Berger et al., Physiological and Therapeutic Roles of Peroxisome Proliferator-Activated Receptors, *Diabetes Technology & Therapeutics*, 2002, 4:163-174.

U.S. Appl. No. 10/791,910.

U.S. Appl. No. 10/792,346.

U.S. Appl. No. 10/791,979.

U.S. Appl. No. 10/700,909.

U.S. Appl. No. 10/639,900.

Cholesterol Drugs May Reverse MS Symptoms, Studies in Mice show statins may treat Multiple Sclerosis—CNN.com/Health, Wednesday, Nov. 6, 2002 posted: 4:30 PM EST (2130 GMT).

D. Grady, Health, Antiocholesterol Drug Found to Help Paralytic Mice,www.nytimes.com/2002/11/07/health/07DRUG.html.

S. Youssef et al., Atorvastatin, a HMG-CoA Reductase Inhibitor, Promotes a Th2 Bias and Reversal of Paralysis in Chronic Relapsing Autoimmune Encephalomyelitis, *Neurology* 58 Apr. 2002 (Suppl 3), A384-A385.

M. Soilu-Hanninen et al., Semliki Forest Virus Infects Mouse Brain Endothelial Cells and Causes Blood-Brain Barrier Damage, *Journal of Virology*, Oct. 1994, 6291-6298.

Chapter 15 Animal Model for Autoimmune and Inflammatory Disease, Unit 15.1 Experimental Autoimmune Encephalomytelitis in the Mouse, *Current Protocols in Immunology*, Nov. 6, 2002.

J. Pope et al., Flow Cytometric and Functional Analyses of Central Nervous System-Infiltrating Cells in SJL/J Mice with Theiler's Virus-Induced Demyelinating Disease—Evidence for a CD4+ T Cell-Mediated Pathology, *The Journal of Immunology* 4050-4058.

H. Butzkueven et al., LIF receptor signaling limits immune-mediated demyelination by enhancing oligodendrocyte survival, *2002 Nature Publishing Group- Nature Medicine*, 8:6 613-619 (Jun. 2002).

I. Grewal et al., CD62L Is Required on Effector Cells for Local Interactions in the CNS to cause Myelin Damage in Experimental Allergic Encephalomyelitis, *Immunity*, 14:291-302 (Mar. 2001).

E. Tran et al., Induction of experimental autoimmune encephalomyelitis in C57BL/6 mice deficient in either the chemokine macrophage inflammatory protein -1α or its CCR5 Receptor, *Eur. J. Immunol.*, 30:1410-1415 (2000).

F. Giubilei et al., Blood cholesterol and MRI activity in first clinical episode suggestive of multiple sclerosis, *Aeta Neurol Scand*, 106:109-112 (2002).

R.O. Weller, Neuropathology & Applied Neurobiology, *Blackwell Scientific Publications*, 20:2 Apr. 1994.

R. Berkow et al., The Merck Manual of Medical Information—Home Edition, *Pocket Books*, Title of Chapter 68 347-350 (1997).

Pelfrey, C., Actrims—Ectrims 2002 (Part II), Baltimore, MD USA, Sep. 18-21, 2002, *The Investigational Drugs Database Alerts*.

P. Reaney, Cholesterol Drugs may help MS Patients, *Yahoo Financial News*, Wednesday, Nov. 6, 2002 pm ET.

H. Wekerle, Tackling Multiple Sclerosis, *Nature*, 420:39-40 (Nov. 7, 2002).

S. Youssef et al., The HMG-CoA reductase inhibitor, atorvastatin, promotes a Th2 bias and reverses paralysis in central nervous system autoimmune disease, *Nature*, 420:78-84 Nov. 7, 2002.

Shestopalov, A.M. et al., Cyclization of Nitriles .XI. Synthesis and reactions of 3-Amino-2-Carboxythieno [2,3-b]-Pyridines, *Zhurnal Organicheskoi Khimii*, 20:9 1818-1827.

Shestopalov, A. M. et al., Cyclization of Nitriles .XIX. Synthesis and reactions of the derivatives of 2-oxo-and 2-thioxo-2,5,6,7-Tetrahydro-1H-Pyrindines, *Zhurnal Organicheskoi Khimii* 22:6 1163-1168.

Luis Gruberg, MD, "Inflammatory Markers in Acute Coronary Syndromes: C-reactive Protein (CRP) and Chlamydia," American Heart Association Scientific Sessions 2000.

T. Kosoglou et al., "CoAdministration of Simvastatin and Ezetimibe Leads to Significant Reduction in LDL-Cholesterol", Proceedings of 3rd International Congress on Coronary, Artery Disease from Prevention to Intervention, Lyon, France p. 271 (2000), XP008027568.

International Search Report for PCT/US 03/35027 (CV01679), dated Apr. 7, 2004—5 Pages.

Margaret Van Heek et al., "Ezetimibe selectivity inhibits intestinal cholesterol absorption in rodents in the presence and absence of exocrine pancreatic function", British Journal of Pharmacology, vol. 134, pp. 409-417 (2001).

\* cited by examiner

METHODS AND THERAPEUTIC COMBINATIONS FOR THE TREATMENT OF DEMYELINATION

CROSS-REFERENCE TO RELATED APPLICATIONS

This application claims the benefit of priority from U.S. Provisional Patent Application Ser. No. 60/493,318, filed Aug. 7, 2003 and U.S. Provisional Patent Application Ser. No. 60/424,165, filed Nov. 6, 2002.

BACKGROUND OF THE INVENTION

1. Field of the Invention

The present invention relates to methods and therapeutic combinations for treating and preventing demyelination in a subject comprising the administration of sterol absorption inhibitor(s).

2. Description

Nerve fibers are wrapped with many layers of insulation known as the myelin sheath. Like insulation around an electrical wire, the myelin sheath permits electrical impulses to be conducted along the nerve fiber with speed and accuracy. When normal development of the myelin is impaired (for example in subjects having Tay-Sachs disease, Niemann-Pick disease, Gaucher's disease and Hurler's syndrome), permanent, extensive neurological defects can result. Also, the myelin sheath can be damaged by stroke, inflammation, immune diseases, metabolic disorders, poison or drugs. If the sheath is able to regenerate itself, normal nerve function can be partially or fully restored. If demyelination is extensive, the underlying nerve can die and cause irreversible damage. Demyelination in the central nervous system (brain and spinal cord) occurs in several primary demyelinating diseases, such as multiple sclerosis, acute disseminated encephalomyelitis, adrenoleukodystrophy, adrenomyeloneuropathy, Leber's hereditary optic atrophy and HTLV-associated myelopathy.

Multiple sclerosis ("MS") is characterized by the loss of patches of myelin in the nerves of the eye, brain and/or spinal cord. It is believed that the body produces antibodies against its own myelin that provoke inflammation and damage the myelin sheath. Heredity and environment appear to play some role in the disease, although it is believed that a virus or unknown antigen somehow triggers the autoimmune process. Symptoms depend upon the area affected. Demyelination in nerve pathways that bring signals to muscles can produce problems with movement (motor symptoms), such as weakness, clumsiness, difficulty in walking or maintaining balance, tremor, double vision, problems with bladder or bowel control, stiffness, unsteadiness or unusual tiredness. Demyelination in nerve pathways that bring signals to the brain can cause sensory symptoms, such as numbness, tingling, dysesthesias, visual disturbances, sexual dysfunction, dizziness or vertigo. Magnetic resonance imaging (MRI) can reveal areas of the brain that have lost myelin, and may even distinguish areas of recent demyelination from areas that occurred some time ago.

Treatments for multiple sclerosis include injection with beta-interferon, which can decrease the frequency and occurrence of flare-ups and slow the progression to disability; injection with glatiramer acetate, which can reduce the frequency of relapses; or administration of corticosteroids, such as prednisone, to relieve acute symptoms. Recently, statins such as simvastatin and atorvastatin (HMG CoA reductase inhibitors) have been studied for their immunomodulatory effects in treating MS. C. Pelfrey, "ACTRIMS-ECTRIMS 2002 (Part II)", IDDB Meeting Report, Sep. 18-21, 2002 Baltimore, Md., USA, (Oct. 3, 2002).

There is a need in the art for improved compositions and treatments for demyelination and associated diseases such as multiple sclerosis.

SUMMARY OF THE INVENTION

In one embodiment, there is provided a method of treating or preventing demyelination in a subject, comprising the step of administering to a subject in need of such treatment an effective amount of at least one sterol absorption inhibitor or a pharmaceutically acceptable salt or solvate thereof.

In another embodiment, there is provided a method of treating or preventing multiple sclerosis in a subject, comprising the step of administering to a subject in need of such treatment an effective amount of at least one sterol absorption inhibitor or a pharmaceutically acceptable salt or solvate thereof.

A method of treating or preventing demyelination in a subject is provided, comprising the step of administering to a subject in need of such treatment an effective amount of at least one sterol absorption inhibitor represented by Formula (II) below:

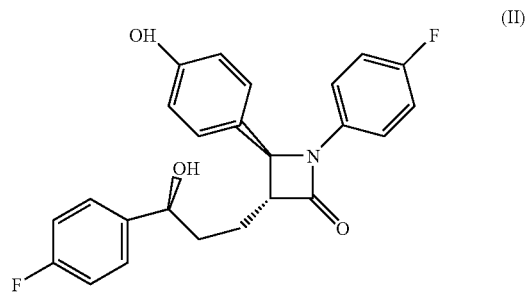

or a pharmaceutically acceptable salt or solvate thereof.

In another embodiment, the present invention provides a composition comprising: (a) at least one sterol absorption inhibitor or a pharmaceutically acceptable salt or solvate thereof and (b) at least one antidemyelination agent.

Therapeutic combinations also are provided comprising: (a) a first amount of at least one sterol absorption inhibitor or a pharmaceutically acceptable salt or solvate thereof; and (b) a second amount of at least one antidemyelination agent, wherein the first amount and the second amount together comprise a therapeutically effective amount for the treatment or prevention of demyelination in a subject.

Pharmaceutical compositions for the treatment or prevention of demyelination in a subject, comprising a therapeutically effective amount of the above compounds, compositions or therapeutic combinations and a pharmaceutically acceptable carrier also are provided.

Other than in the operating examples, or where otherwise indicated, all numbers expressing quantities of ingredients, reaction conditions, and so forth used in the specification and claims are to be understood as being modified in all instances by the term "about."

DETAILED DESCRIPTION

According to F. Giubilei et al., "Blood Cholesterol and MRI Activity in First Clinical Episode Suggestive of Multiple Sclerosis", Acta Neurol Scand 2002: 106: 109-112, 111, a significant correlation was found between MS disease activity and both total and LDL (low density lipoprotein) cholesterol levels. Lesions formed by demyelination are characterized by the presence of foamy macrophages containing cholesterol esters. J. Newcombe et al., "Low Density Lipoprotein Uptake by Macrophages in Multiple Sclerosis Plaques: Implication for Pathogenesis", Neuropathol. Appl. Neurobiol. 1994: 20:152-62, 152. There is evidence of early involvement of LDL in the development of MS lesions. F. Giubilei at 111. A large proportion of the plasma LDL enters the parenchyma of MS plaques as a result of blood-brain barrier damage and is oxidatively modified in the lesion. Id. Lipid peroxidation and oxidized LDL uptake by infiltrating macrophages or microglial cells in early stages of MS plaque development may play an important role in demyelination. Id.

U.S. Pat. Nos. 5,767,115, 5,624,920, 5,668,990, 5,656,624 and 5,688,787, respectively, disclose hydroxy-substituted azetidinone compounds and substituted β-lactam compounds useful for inhibiting the absorption of cholesterol, thereby lowering cholesterol levels and/or inhibiting the formation of cholesterol-containing lesions in mammalian arterial walls. U.S. Pat. Nos. 5,846,966 and 5,661,145, respectively, disclose hydroxy-substituted azetidinone compounds or substituted β-lactam compounds in combination with HMG CoA reductase inhibitors for preventing or treating atherosclerosis and reducing plasma cholesterol levels. Such compounds can also be useful in lowering C-reactive protein levels in subjects.

According to the present invention, these and other sterol absorption inhibitors discussed in detail below can be useful in preventing or treating demyelination and its associated conditions, such as primary demyelinating diseases including but not limited to multiple sclerosis, acute disseminated encephalomyelitis, adrenoleukodystrophy, adrenomyeloneuropathy, Leber's hereditary optic atrophy and HTLV-associated myelopathy, and other conditions characterized by demyelination such as Tay-Sachs disease, Niemann-Pick disease, Gaucher's disease and Hurler's syndrome; or stroke, inflammation, immune diseases, metabolic disorders, poison or drugs.

In one embodiment, the present invention is directed to compositions, pharmaceutical compositions, therapeutic combinations, kits and methods of treatment using the same comprising at least one (one or more) sterol absorption inhibitor(s). Suitable sterol absorption inhibitors include substituted azetidinone sterol absorption inhibitors, substituted β-lactam sterol absorption inhibitors or combinations thereof as discussed in detail below. As used herein, "sterol absorption inhibitor" means a compound capable of inhibiting the absorption of one or more sterols, including but not limited to cholesterol, phytosterols (such as sitosterol, campesterol, stigmasterol and avenosterol), when administered in a therapeutically effective (sterol absorption inhibiting) amount to a subject, such as a mammal or human. Other useful compositions, pharmaceutical compositions, therapeutic combinations, kits and methods of treatment using the same comprise at least one (one or more) 5α-stanol absorption inhibitor(s). As used herein, "5α-stanol absorption inhibitor" means a compound capable of inhibiting the absorption of one or more 5α-stanols (such as cholestanol, 5α-campestanol, 5α-sitostanol), when administered in a therapeutically effective (5α-stanol absorption inhibiting) amount to a subject, such as a mammal or human.

In a preferred embodiment, sterol or 5α-stanol absorption inhibitors useful in the compositions, therapeutic combinations and methods of the present invention are represented by Formula (I) below:

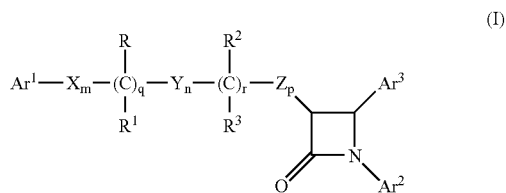

or a pharmaceutically acceptable salt thereof or a solvate thereof, wherein, in Formula (I) above:

$Ar^1$ and $Ar^2$ are independently selected from the group consisting of aryl and $R^4$-substituted aryl;

$Ar^3$ is aryl or $R^5$-substituted aryl;

X, Y and Z are independently selected from the group consisting of —$CH_2$—, —CH(lower alkyl)- and —C(dilower alkyl)-;

R and $R^2$ are independently selected from the group consisting of —$OR^6$, —O(CO)$R^6$, —O(CO)$OR^9$ and —O(CO)$NR^6R^7$;

$R^1$ and $R^3$ are independently selected from the group consisting of hydrogen, lower alkyl and aryl;

q is 0 or 1; r is 0 or 1; m, n and p are independently selected from 0, 1, 2, 3 or 4; provided that at least one of q and r is 1, and the sum of m, n, p, q and r is 1, 2, 3, 4, 5 or 6; and provided that when p is 0 and r is 1, the sum of m, q and n is 1, 2, 3, 4 or 5;

$R^4$ is 1-5 substituents independently selected from the group consisting of lower alkyl, —$OR^6$, —O(CO)$R^6$, —O(CO)$OR^9$, —O($CH_2$)$_{1-5}OR^6$, —O(CO)$NR^6R^7$, —$NR^6R^7$, —$NR^6$(CO)$R^7$, —$NR^6$(CO)$OR^9$, —$NR^6$(CO)$NR^7R^8$, —$NR^6SO_2R^9$, —COO$R^6$, —CON$R^6R^7$, —COR$^6$, —$SO_2NR^6R^7$, S(O)$_{0-2}R^9$, —O($CH_2$)$_{1-10}$—COOR$^6$, —O($CH_2$)$_{1-10}$, OCON$R^6R^7$, -(lower alkylene)COO$R^6$, —CH=CH—COO$R^6$, —$CF_3$, —CN, —$NO_2$ and halogen;

$R^5$ is 1-5 substituents independently selected from the group consisting of —$OR^6$, —O(CO)$R^6$, —O(CO)$OR^9$, —O($CH_2$)$_{1-5}R^6$, —O(CO)$NR^6R^7$, —$NR^6R^7$, —$NR^6$(CO)$R^7$, —$NR^6$(CO)$OR^9$, —$NR^6$(CO)$NR^7R^8$, —$NR^6SO_2R^9$, —COO$R^6$, —CON$R^6R^7$, —COR$^6$, —$SO_2NR^6R^7$, S(O)$_{0-2}R^9$, —O($CH_2$)$_{1-10}$—COOR$^6$, —O($CH_2$)$_{1-10}$CON$R^6R^7$, -(lower alkylene)COO$R^6$ and —CH=CH—COO$R^6$;

$R^6$, $R^7$ and $R^8$ are independently selected from the group consisting of hydrogen, lower alkyl, aryl and aryl-substituted lower alkyl; and $R^9$ is lower alkyl, aryl or aryl-substituted lower alkyl.

Preferably, $R^4$ is 1-3 independently selected substituents, and $R^5$ is preferably 1-3 independently selected substituents.

In a preferred embodiment, a sterol or 5α-stanol absorption inhibitor of Formula (I) useful in the compositions, therapeutic combinations and methods of the present invention is represented by Formula (II) (ezetimibe) below:

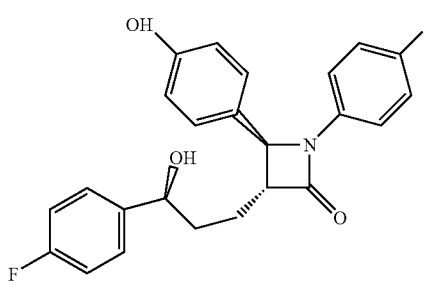

(II)

or a pharmaceutically acceptable salt or solvate thereof. The compound of Formula (II) can be in anhydrous or hydrated form.

As used herein, the term "alkyl" or "lower alkyl" means straight or branched alkyl chains having from 1 to 6 carbon atoms and "alkoxy" means alkoxy groups having 1 to 6 carbon atoms. Non-limiting examples of lower alkyl groups include, for example methyl, ethyl, propyl, and butyl groups. Where an alkyl chain joins two other variables and is therefore bivalent, the term alkylene is used.

"Aryl" means an aromatic monocyclic or multicyclic ring system comprising about 6 to about 14 carbon atoms, preferably about 6 to about 10 carbon atoms, such as phenyl, naphthyl, indenyl, tetrahydronaphthyl or indanyl.

The statements wherein, for example, R, $R^1$, $R^2$ and $R^3$ are said to be independently selected from a group of substituents mean that R, $R^1$, $R^2$ and $R^2$ are each independently selected, but also that where an R, $R^1$, $R^2$ and $R^3$ variable occurs more than once in a molecule, each occurrence is independently selected (e.g., if is —$OR^6$, wherein $R^6$ is hydrogen, $R^2$ can be —$OR^6$ wherein $R^6$ is lower alkyl). Those skilled in the art will recognize that the size and nature of the substituent(s) will affect the number of substituents that can be present.

Compounds of Formula I can be prepared by a variety of methods well known to those skilled in the art, for example such as are disclosed in U.S. Pat. Nos. 5,631,365, 5,767,115, 5,846,966, 6,207,822, PCT Patent Application No. 02/079174 and PCT Patent Application WO 93/02048, each of which is incorporated herein by reference, and in the Example below.

Alternative sterol absorption inhibitors useful in the compositions, therapeutic combinations and methods of the present invention are represented by Formula (III) below:

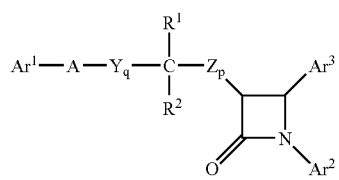

(III)

or a pharmaceutically acceptable salt thereof or a solvate thereof, wherein, in Formula (III) above:

$Ar^1$ is $R^3$-substituted aryl;
$Ar^2$ is $R^4$-substituted aryl;
$Ar^3$ is $R^5$-substituted aryl;
Y and Z are independently selected from the group consisting of —$CH_2$—, —CH(lower alkyl)- and —C(dilower alkyl)-;

A is selected from —O—, —S—, —S(O)— or —$S(O)_2$—;
$R^1$ is selected from the group consisting of —$OR^6$, —$O(CO)R^6$, —$O(CO)OR^9$ and —$O(CO)NR^6R^7$; $R^2$ is selected from the group consisting of hydrogen, lower alkyl and aryl; or $R^1$ and $R^2$ together are =O;
q is 1, 2 or 3;
p is 0, 1, 2, 3 or 4;
$R^5$ is 1-3 substituents independently selected from the group consisting of —$OR^6$, —$O(CO)R^6$, —$O(CO)OR^9$, —$O(CH_2)_{1-5}OR^6$, —$O(CO)NR^6R^7$, —$NR^6R^7$, —$NR^6(CO)R^7$, —$NR^6(CO)OR$, —$NR^6(CO)NR^7R$, —$NR^6SO_2$-lower alkyl, —$NR^6SO_2$-aryl, —$CONR^6R^7$, —$COR^6$, —$SO_2NR^6R^7$, —$S(O)_{0-2}$-alkyl, $S(O)_{0-2}$-aryl, —$O(CH_2)_{1-10}$—$COOR^6$, —$O(CH_2)_{1-10}CONR^6R^7$ o-halogeno, m-halogeno, o-lower alkyl, m-lower alkyl, -(lower alkylene)-$COOR^6$, and —CH=CH—$COOR^6$;

$R^3$ and $R^4$ are independently 1-3 substituents independently selected from the group consisting of $R^5$, hydrogen, p-lower alkyl, aryl, —$NO_2$, —$CF_3$ and p-halogeno;

$R^6$, $R^7$ and $R^8$ are independently selected from the group consisting of hydrogen, lower alkyl, aryl and aryl-substituted lower alkyl; and $R^9$ is lower alkyl, aryl or aryl-substituted lower alkyl.

Methods for making compounds of Formula III are well known to those skilled in the art. Non-limiting examples of suitable methods are disclosed in U.S. Pat. No. 5,688,990, which is incorporated herein by reference.

In another embodiment, sterol absorption inhibitors useful in the compositions, therapeutic combinations and methods of the present invention are represented by Formula (IV):

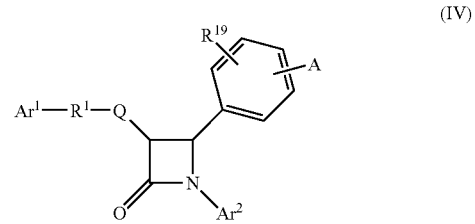

(IV)

or a pharmaceutically acceptable salt thereof or a solvate thereof, wherein, in Formula (IV) above:

A is selected from the group consisting of $R^2$-substituted heterocycloalkyl, $R^2$-substituted heteroaryl, $R^2$-substituted benzofused heterocycloalkyl, and $R^2$-substituted benzofused heteroaryl;

$Ar^1$ is aryl or $R^3$-substituted aryl;
$Ar^2$ is aryl or $R^4$-substituted aryl;
Q is a bond or, with the 3-position ring carbon of the azetidinone, forms the spiro group

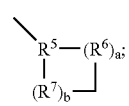

and
$R^1$ is selected from the group consisting of:
—$(CH_2)_q$—, wherein q is 2-6, provided that when Q forms a spiro ring, q can also be zero or 1;
—$(CH_2)_e$-G-$(CH_2)_r$—, wherein G is —O—, —C(O)—, phenylene, —$NR^8$— or —$S(O)_{0-2}$—, e is 0-5 and r is 0-5, provided that the sum of e and r is 1-6;

—($C_2$-$C_6$ alkenylene)-; and

—($CH_2$)$_f$—V—($CH_2$)$_g$—, wherein V is $C_3$-$C_6$ cycloalkylene, f is 1-5 and g is 0-5, provided that the sum of f and g is 1-6;

$R^5$ is selected from:

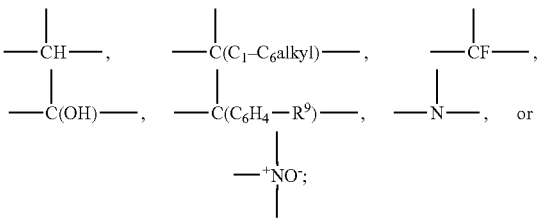

$R^6$ and $R^7$ are independently selected from the group consisting of —$CH_2$—, —CH($C_1$-$C_6$ alkyl)-, —C(di-($C_1$-$C_6$) alkyl), —CH=CH— and —C($C_1$-$C_6$ alkyl)=CH—; or $R^5$ together with an adjacent $R^6$, or $R^5$ together with an adjacent $R^7$, form a —CH=CH— or a —CH=C($C_1$-$C_6$ alkyl)-group;

a and b are independently 0, 1, 2 or 3, provided both are not zero; provided that when $R^6$ is —CH=CH— or —C($C_1$-$C_6$ alkyl)=CH—, a is 1; provided that when $R^7$ is —CH=CH— or —C($C_1$-$C_6$ alkyl)=CH—, b is 1; provided that when a is 2 or 3, the $R^6$'s can be the same or different; and provided that when b is 2 or 3, the $R^7$'s can be the same or different;

and when Q is a bond, $R^1$ also can be selected from:

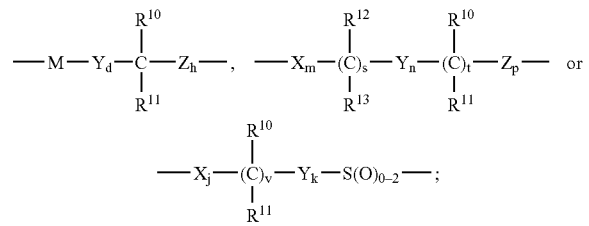

where M is —O—, —S—, —S(O)— or —S(O)$_2$—;

X, Y and Z are independently selected from the group consisting of —$CH_2$—, —CH($C_1$-$C_6$ alkyl)- and —C(di-($C_1$-$C_6$)alkyl);

$R^{10}$ and $R^{12}$ are independently selected from the group consisting of —$OR^{14}$, —O(CO)$R^{14}$, —O(CO)$OR^{16}$ and —O(CO)$NR^{14}R^{15}$;

$R^{11}$ and $R^{13}$ are independently selected from the group consisting of hydrogen, ($C_1$-$C_6$)alkyl and aryl; or $R^{10}$ and $R^{11}$ together are =O, or $R^{12}$ and $R^{13}$ together are =O;

d is 1, 2 or 3;

h is 0, 1, 2, 3 or 4;

s is 0 or 1; t is 0 or 1; m, n and p are independently 0-4; provided that at least one of s and t is 1, and the sum of m, n, p, s and t is 1-6; provided that when p is 0 and t is 1, the sum of m, s and n is 1-5; and provided that when p is 0 and s is 1, the sum of m, t and n is 1-5;

v is 0 or 1;

j and k are independently 1-5, provided that the sum of j, k and v is 1-5;

$R^2$ is 1-3 substituents on the ring carbon atoms selected from the group consisting of hydrogen, ($C_1$-$C_{10}$)alkyl, ($C_2$-$C_{10}$)alkenyl, ($C_2$-$C_{10}$)alkynyl, ($C_3$-$C_6$)cycloalkyl, ($C_3$-$C_6$)cycloalkenyl, $R^{17}$-substituted aryl, $R^{17}$-substituted benzyl, $R^{17}$-substituted benzyloxy, $R^{17}$-substituted aryloxy, halogeno, —$NR^{14}R^{15}$, $NR^{14}R^{15}$($C_1$-$C_6$ alkylene)-, $NR^{14}R^{15}$C(O)($C_1$-$C_6$ alkylene)-, —NHC(O)$R^{16}$, OH, $C_1$-$C_6$ alkoxy, —OC(O)$R^{16}$, —$COR^{14}$, hydroxy($C_1$-$C_6$)alkyl, ($C_1$-$C_6$)alkoxy($C_1$-$C_6$)alkyl, $NO_2$, —S(O)$_{0-2}R^{16}$, —$SO_2NR^{14}R^{15}$ and —($C_1$-$C_6$ alkylene)$COOR^{14}$; when $R^2$ is a substituent on a heterocycloalkyl ring, $R^2$ is as defined, or is =O or

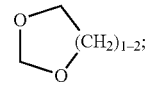

and, where $R^2$ is a substituent on a substitutable ring nitrogen, it is hydrogen, ($C_1$-$C_6$)alkyl, aryl, ($C_1$-$C_6$)alkoxy, aryloxy, ($C_1$-$C_6$)alkylcarbonyl, arylcarbonyl, hydroxy, —($CH_2$)$_{1-6}$ $CONR^{18}R^{18}$,

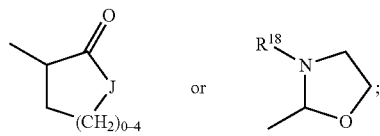

wherein J is —O—, —NH—, —$NR^{18}$— or —$CH_2$—;

$R^3$ and $R^4$ are independently selected from the group consisting of 1-3 substituents independently selected from the group consisting of ($C_1$-$C_6$)alkyl, —$OR^{14}$, —O(CO)$R^{14}$, —O(CO)$OR^{16}$, —O($CH_2$)$_{1-5}OR^{14}$, —O(CO)$NR^{14}R^{15}$, —$NR^{14}R^{15}$, —$NR^{14}$(CO)$R^{15}$, —$NR^{14}$(CO)$OR^{16}$, —$NR^{14}$(CO)$NR^{15}R^{19}$, —$NR^{14}SO_2R^{16}$, —$COOR^{14}$, —$CONR^{14}R^{15}$, —$COR^{14}$, —$SO_2NR^{14}R^{15}$, S(O)$_{0-2}R^{16}$, O($CH_2$)$_{1-10}$—$COOR^{14}$, —O($CH_2$)$_{1-10}CONR^{14}R^{15}$, —($C_1$-$C_6$ alkylene)-$COOR^{14}$, —CH=CH—$COOR^{14}$, —$CF_3$, —CN, —$NO_2$, and halogen;

$R^8$ is hydrogen, ($C_1$-$C_6$)alkyl, aryl($C_1$-$C_6$)alkyl, —C(O)$R^{14}$ or —$COOR^{14}$;

$R^9$ and $R^{17}$ are independently 1-3 groups independently selected from the group consisting of hydrogen, ($C_1$-$C_6$) alkyl, ($C_1$-$C_6$)alkoxy, —COOH, $NO_2$, —$NR^{14}R^{15}$, OH and halogeno;

$R^{14}$ and $R^{15}$ are independently selected from the group consisting of hydrogen, ($C_1$-$C_6$)alkyl, aryl and aryl-substituted ($C_1$-$C_6$)alkyl;

$R^{16}$ is ($C_1$-$C_6$)alkyl, aryl or $R^{17}$-substituted aryl;

$R^{18}$ is hydrogen or ($C_1$-$C_6$)alkyl; and $R^{19}$ is hydrogen, hydroxy or ($C_1$-$C_6$)alkoxy.

Methods for making compounds of Formula IV are well known to those skilled in the art. Non-limiting examples of suitable methods are disclosed in U.S. Pat. No. 5,656,624, which is incorporated herein by reference.

In another embodiment, sterol absorption inhibitors useful in the compositions, therapeutic combinations and methods of the present invention are represented by Formula (V):

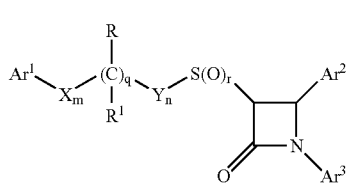

(V)

or a pharmaceutically acceptable salt thereof or a solvate thereof, wherein, in Formula (V) above:

$Ar^1$ is aryl, $R^{10}$-substituted aryl or heteroaryl;

$Ar^2$ is aryl or $R^4$-substituted aryl;

$Ar^3$ is aryl or $R^5$-substituted aryl;

X and Y are independently selected from the group consisting of —$CH_2$—, —CH(lower alkyl)- and —C(dilower alkyl)-;

R is —$OR^6$, —$O(CO)R^6$, —$O(CO)OR^9$ or —$O(CO)NR^6R^7$; $R^1$ is hydrogen, lower alkyl or aryl; or R and $R^1$ together are =O;

q is 0 or 1;

r is 0, 1 or 2;

m and n are independently 0, 1, 2, 3, 4 or 5; provided that the sum of m, n and q is 1, 2, 3, 4 or 5;

$R^5$ is 1-5 substituents independently selected from the group consisting of lower alkyl, —$OR^6$, —$O(CO)R^6$, —$O(CO)OR^9$, —$O(CH_2)_{1-5}OR^6$, —$O(CO)NR^6R^7$, —$NR^6R^7$, —$NR^6(CO)R^7$, —$NR^6(CO)OR^9$, —$NR^6(CO)NR^7R^8$, —$NR^6SO_2R^9$, —$COOR^6$, —$CONR^6R^7$, —$COR^6$, —$SO_2NR^6R^7$, $S(O)_{0-2}R^9$, —$O(CH_2)_{1-10}COOR^6$, —$O(CH_2)_{1-10}CONR^6R^7$, -(lower alkylene)$COOR^6$ and —CH=CH—$COOR^6$;

$R^5$ is 1-5 substituents independently selected from the group consisting of —$OR^6$, —$O(CO)R^6$, —$O(CO)OR^9$, —$O(CH_2)_{1-5}OR^6$, —$O(CO)NR^6R^7$, —$NR^6R^7$, —$NR^6(CO)R^7$, —$NR^6(CO)OR^9$, —$NR^6(CO)NR^7R^8$, —$NR^6SO_2R^9$, —$COOR^6$, —$CONR^6R^7$, —$COR^6$, —$SO_2NR^6R^7$, $S(O)_{0-2}R^9$, —$O(CH_2)_{1-10}COOR^6$, —$O(CH_2)_{1-10}CONR^6R^7$, —$CF_3$, —CN, —$NO_2$, halogen, -(lower alkylene)$COOR^6$ and —CH=CH—$COOR^6$;

$R^6$, $R^7$ and $R^8$ are independently selected from the group consisting of hydrogen, lower alkyl, aryl and aryl-substituted lower alkyl;

$R^9$ is lower alkyl, aryl or aryl-substituted lower alkyl; and $R^{10}$ is 1-5 substituents independently selected from the group consisting of lower alkyl, —$OR^6$, —$O(CO)R^6$, —$O(CO)OR^9$, —$O(CH_2)_{1-5}OR^6$, —$O(CO)NR^6R^7$, —$NR^6R^7$, —$NR^6(CO)R^7$, —$NR^6(CO)OR^9$, —$NR^6(CO)NR^7R^8$, —$NR^6SO_2R^9$, —$COOR^6$, —$CONR^6R^7$, —$COR^6$, —$SO_2NR^6R^7$, —$S(O)_{0-2}R^9$, —$O(CH_2)_{1-10}COOR^6$; —$O(CH_2)_{1-10}CONR^6R^7$, —$CF_3$, —CN, —$NO_2$ and halogen.

Methods for making compounds of Formula V are well known to those skilled in the art. Non-limiting examples of suitable methods are disclosed in U.S. Pat. No. 5,624,920, which is incorporated herein by reference.

In another embodiment, sterol absorption inhibitors useful in the compositions, 0.5 therapeutic combinations and methods of the present invention are represented by Formula (VI):

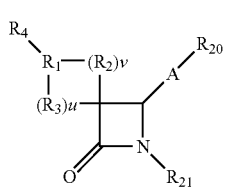

(VI)

or a pharmaceutically acceptable salt thereof or a solvate thereof, wherein:

$R_1$ is

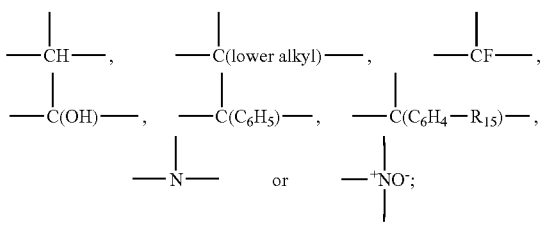

$R_2$ and $R_3$ are independently selected from the group consisting of: —$CH_2$—, —CH(lower alkyl)-, —C(di-lower alkyl)-, —CH=CH— and —C(lower alkyl)=CH—; or $R_1$ together with an adjacent $R_2$, or $R_1$ together with an adjacent $R_3$, form a —CH=CH— or a —CH=C(lower alkyl)- group;

u and v are independently 0, 1, 2 or 3, provided both are not zero; provided that when $R_2$ is —CH=CH— or —C(lower alkyl)=CH—, v is 1; provided that when $R_3$ is CH=CH— or —C(lower alkyl)=CH—, u is 1; provided that when v is 2 or 3, the $R_2$'s can be the same or different; and provided that when u is 2 or 3, the $R_3$'s can be the same or different;

$R_4$ is selected from B—$(CH_2)_mC(O)$—, wherein m is 0, 1, 2, 3, 4 or 5; B—$(CH_2)_q$—, wherein q is 0, 1, 2, 3, 4, 5 or 6; B—$(CH_2)_e$-Z-$(CH_2)_r$—, wherein Z is —O—, —C(O)—, phenylene, —$N(R_8)$— or —$S(O)_{0-2}$—, e is 0, 1, 2, 3, 4 or 5 and r is 0, 1, 2, 3, 4 or 5, provided that the sum of e and r is 0, 1, 2, 3, 4, 5 or 6; B—($C_2$-$C_6$ alkenylene)-; B—($C_4$-$C_6$ alkadienylene)-; B—$(CH_2)_t$-Z-($C_2$-$C_6$ alkenylene)-, wherein Z is as defined above, and wherein t is 0, 1, 2 or 3, provided that the sum of t and the number of carbon atoms in the alkenylene chain is 2, 3, 4, 5 or 6; B—$(CH_2)_f$—V—$(CH_2)_g$—, wherein V is $C_3$-$C_6$ cycloalkylene, f is 1, 2, 3, 4 or 5 and g is 0, 1, 2, 3, 4 or 5, provided that the sum of f and g is 1, 2, 3, 4, 5 or 6; B—$(CH_2)_t$—V—($C_2$-$C_6$ alkenylene)- or B—($C_2$-$C_6$ alkenylene)-V—$(CH_2)_t$—, wherein V and t are as defined above, provided that the sum of t and the number of carbon atoms in the alkenylene chain is 2, 3, 4, 5 or 6;

B—$(CH_2)_a$-Z-$(CH_2)_b$—V—$(CH_2)_d$—, wherein Z and V are as defined above and a, b and d are independently 0, 1, 2, 3, 4, 5 or 6, provided that the sum of a, b and d is 0, 1, 2, 3, 4, 5 or 6; or T-$(CH_2)_s$—, wherein T is cycloalkyl of 3-6 carbon atoms and s is 0, 1, 2, 3, 4, 5 or 6; or $R_1$ and $R_4$ together form the group

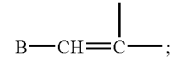

B is selected from indanyl, indenyl, naphthyl, tetrahydronaphthyl, heteroaryl or W-substituted heteroaryl, wherein heteroaryl is selected from the group consisting of pyrrolyl, pyridinyl, pyrimidinyl, pyrazinyl, triazinyl, imidazolyl, thiazolyl, pyrazolyl, thienyl, oxazolyl and furanyl, and for nitrogen-containing heteroaryls, the N-oxides thereof, or

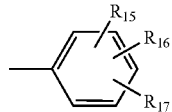

W is 1 to 3 substituents independently selected from the group consisting of lower alkyl, hydroxy lower alkyl, lower alkoxy, alkoxyalkyl, alkoxyalkoxy, alkoxycarbonylalkoxy, (lower alkoxyimino)-lower alkyl, lower alkanedioyl, lower alkyl lower alkanedioyl, allyloxy, —CF$_3$, —OCF$_3$, benzyl, R$_7$-benzyl, benzyloxy, R$_7$-benzyloxy, phenoxy, R$_7$-phenoxy, dioxolanyl, NO$_2$, —N(R$_8$)(R$_9$), N(R$_8$)(R$_9$)-lower alkylene-, N(R$_8$)(R$_9$)-lower alkylenyloxy-, OH, halogeno, —CN, —N$_3$, —NHC(O)OR$_{10}$, —NHC(O)R$_{10}$, R$_{11}$O$_2$SNH—, (R$_{11}$O$_2$S)$_2$N—, —S(O)$_2$NH$_2$, —S(O)$_{0-2}$R$_8$, tert-butyldimethyl-silyloxymethyl, —C(O)R$_{12}$, —COOR$_{19}$, —CON(R$_8$)(R$_9$), —CH=CHC(O)R$_{12}$, -lower alkylene-C(O)R$_{12}$, R$_{10}$C(O)(lower alkylenyloxy)-, N(R$_8$)(R$_9$)C(O)(lower alkylenyloxy)- and

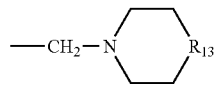

for substitution on ring carbon atoms, and the substituents on the substituted heteroaryl ring nitrogen atoms, when present, are selected from the group consisting of lower alkyl, lower alkoxy, —C(O)OR$_{10}$, —C(O)R$_{10}$, OH, N(R$_8$)(R$_9$)-lower alkylene-, N(R$_8$)(R$_9$)-lower alkylenyloxy-, —S(O)$_2$NH$_2$ and 2-(trimethylsilyl)-ethoxymethyl;

R$_7$ is 1-3 groups independently selected from the group consisting of lower alkyl, lower alkoxy, —COOH, NO$_2$, —N(R$_8$)(R$_9$), OH, and halogeno;

R$_8$ and R$_9$ are independently selected from H or lower alkyl;

R$_{10}$ is selected from lower alkyl, phenyl, R$_7$-phenyl, benzyl or R$_7$-benzyl;

R$_{11}$ is selected from OH, lower alkyl, phenyl, benzyl, R$_7$-phenyl or R$_7$-benzyl;

R$_{12}$ is selected from H, OH, alkoxy, phenoxy, benzyloxy,

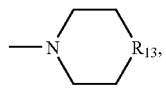

—N(R$_8$)(R$_9$), lower alkyl, phenyl or R$_7$-phenyl;

R$_{13}$ is selected from —O—, —CH$_2$—, —NH—, —N(lower alkyl)- or —NC(O)R$_{19}$;

R$_{15}$, R$_{16}$ and R$_{17}$ are independently selected from the group consisting of H and the groups defined for W; or R$_{15}$ is hydrogen and R$_{16}$ and R$_{17}$, together with adjacent carbon atoms to which they are attached, form a dioxolanyl ring;

R$_{19}$ is H, lower alkyl, phenyl or phenyl lower alkyl; and

R$_{20}$ and R$_{21}$ are independently selected from the group consisting of phenyl, W-substituted phenyl, naphthyl, W-substituted naphthyl, indanyl, indenyl, tetrahydronaphthyl, benzodioxolyl, heteroaryl, W-substituted heteroaryl, benzofused heteroaryl, W-substituted benzofused heteroaryl and cyclopropyl, wherein heteroaryl is as defined above.

Methods for making compounds of Formula VI are well known to those skilled in the art. Non-limiting examples of suitable methods are disclosed in U.S. Pat. No. 5,698,548, which is incorporated herein by reference.

In another embodiment, sterol absorption inhibitors useful in the compositions, therapeutic combinations and methods of the present invention are represented by Formulas (VIIA) and (VIIB):

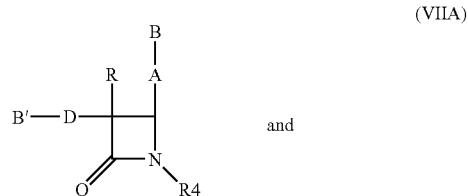

(VIIA)

and

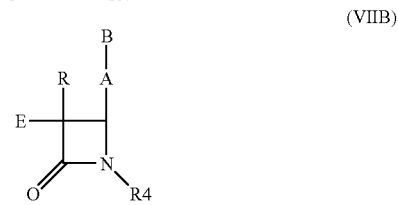

(VIIB)

or a pharmaceutically acceptable salt or solvate thereof, wherein:

A is —CH=CH—, —C≡C— or —(CH$_2$)$_p$— wherein p is 0, 1 or 2;

B is

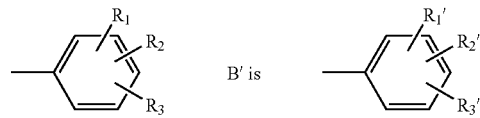

B' is

D is —(CH$_2$)$_m$C(O)— or —(CH$_2$)$_q$— wherein m is 1, 2, 3 or 4 and q is 2, 3 or 4;

E is C$_{10}$ to C$_{20}$ alkyl or —C(O)—(C$_9$ to C$_1$g)-alkyl, wherein the alkyl is straight or branched, saturated or containing one or more double bonds;

R is hydrogen, C$_1$-C$_{15}$ alkyl, straight or branched, saturated or containing one or more double bonds, or B—(CH$_2$)$_r$—, wherein r is 0, 1, 2, or 3;

R$_1$, R$_2$, R$_3$, R$_1'$, R$_2'$, and R$_3'$ are independently selected from the group consisting of hydrogen, lower alkyl, lower alkoxy, carboxy, NO$_2$, NH$_2$, OH, halogeno, lower alkylamino, dilower alkylamino, —NHC(O)OR$_5$, R$_6$O$_2$SNH— and —S(O)$_2$NH$_2$;

R$_4$ is

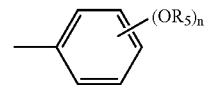

wherein n is 0, 1, 2 or 3;

R$_5$ is lower alkyl; and $R_6$ is OH, lower alkyl, phenyl, benzyl or substituted phenyl wherein the substituents are 1-3 groups independently selected from the group consisting of lower alkyl, lower alkoxy, carboxy, $NO_2$, $NH_2$, OH, halogeno, lower alkylamino and dilower alkylamino; or a pharmaceutically acceptable salt thereof or a solvate thereof.

In another embodiment, sterol absorption inhibitors useful in the compositions and methods of the present invention are represented by Formula (VIII):

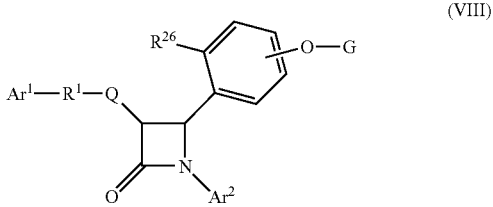

(VIII)

or a pharmaceutically acceptable salt thereof or a solvate thereof, wherein, in Formula (VIII) above, $R^{26}$ is H or $OG^1$;

G and $G^1$ are independently selected from the group consisting of

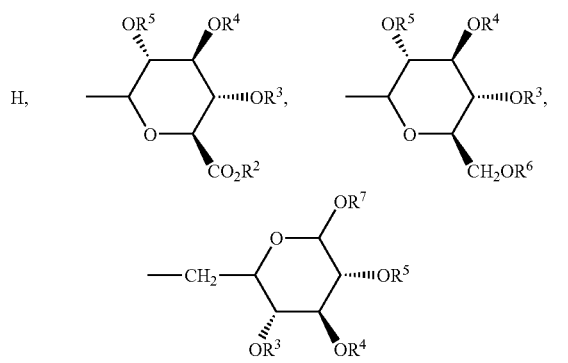

and

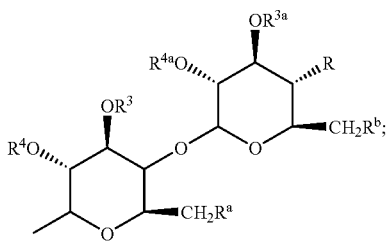

provided that when $R^{26}$ is H or OH, G is not H;

R, $R^a$ and $R^b$ are independently selected from the group consisting of H, —OH, halogeno, —$NH_2$, azido, ($C_1$-$C_6$)alkoxy($C_1$-$C_6$)-alkoxy or —W—$R^{30}$;

W is independently selected from the group consisting of —NH—C(O)—, —O—C(O)—, —O—C(O)—N($R^{31}$)—, —NH—C(O)—N($R^{31}$)— and —O—C(S)—N($R^{31}$)—;

$R^2$ and $R^6$ are independently selected from the group consisting of H, ($C_1$-$C_6$)alkyl, aryl and aryl($C_1$-$C_6$)alkyl;

$R^3$, $R^4$, $R^5$, $R^7$, $R^{3a}$ and $R^{4a}$ are independently selected from the group consisting of H, ($C_1$-$C_6$)alkyl, aryl($C_1$-$C_6$)alkyl, —C(O)($C_1$-$C_6$)alkyl and —C(O)aryl;

$R^{30}$ is selected from the group consisting of $R^{32}$-substituted T, $R^{32}$-substituted-T-($C_1$-$C_6$)alkyl, $R^{32}$-substituted-($C_2$-$C_4$)alkenyl, $R^{32}$-substituted-($C_1$-$C_6$)alkyl, $R^{32}$-substituted-($C_3$-$C_7$)cycloalkyl and $R^{32}$-substituted-($C_3$-$C_7$)cycloalkyl($C_1$-$C_6$)alkyl;

$R^{31}$ is selected from the group consisting of H and ($C_1$-$C_4$) alkyl;

T is selected from the group consisting of phenyl, furyl, thienyl, pyrrolyl, oxazolyl, isoxazolyl, thiazolyl, iosthiazolyl, benzothiazolyl, thiadiazolyl, pyrazolyl, imidazolyl and pyridyl;

$R^{32}$ is independently selected from 1-3 substituents independently selected from the group consisting of halogeno, ($C_1$-$C_4$)alkyl, —OH, phenoxy, —$CF_3$, —$NO_2$, ($C_1$-$C_4$) alkoxy, methylenedioxy, oxo, ($C_1$-$C_4$)alkylsulfanyl, ($C_1$-$C_4$)alkylsulfinyl, ($C_1$-$C_4$)alkylsulfonyl, —N($CH_3$)$_2$, —C(O)—NH($C_1$-$C_4$)alkyl, —C(O)—N(($C_1$-$C_4$)alkyl)$_2$, —C(O)—($C_1$-$C_4$)alkyl, —C(O)—($C_1$-$C_4$)alkoxy and pyrrolidinylcarbonyl; or $R^{32}$ is a covalent bond and $R^{31}$, the nitrogen to which it is attached and $R^{32}$ form a pyrrolidinyl, piperidinyl, N-methyl-piperazinyl, indolinyl or morpholinyl group, or a ($C_1$-$C_4$)alkoxycarbonyl-substituted pyrrolidinyl, piperidinyl, N-methylpiperazinyl, indolinyl or morpholinyl group;

$Ar^1$ is aryl or $R^{10}$-substituted aryl;

$Ar^2$ is aryl or $R^{11}$-substituted aryl;

Q is a bond or, with the 3-position ring carbon of the azetidinone, forms the spiro group

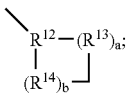

and $R^1$ is selected from the group consisting of

—($CH_2$)$_q$—, wherein q is 2-6, provided that when Q forms a spiro ring, q can also be zero or 1;

—($CH_2$)$_e$-E-($CH_2$)$_r$—, wherein E is —O—, —C(O)—, phenylene, —$NR^{22}$— or —S(O)$_{0-2}$—, e is 0-5 and r is 0-5, provided that the sum of e and r is 1-6;

—($C_2$-$C_6$)alkenylene-; and

—($CH_2$)$_f$—V—($CH_2$)$_g$—, wherein V is $C_3$-$C_6$ cycloalkylene, f is 1-5 and g is 0-5, provided that the sum of f and g is 1-6;

$R^{12}$ is

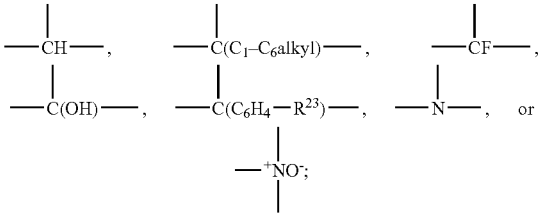

$R^{13}$ and $R^{14}$ are independently selected from the group consisting of

—$CH_2$—, —CH($C_1$-$C_6$ alkyl)-, —C(di-($C_1$-$C_6$)alkyl), —CH=CH— and —C($C_1$-$C_6$ alkyl)=CH—; or $R^{12}$ together with an adjacent $R^{13}$, or $R^{12}$ together with an adjacent $R^{14}$, form a —CH=CH— or a —CH=C($C_1$-$C_6$ alkyl )- group;

a and b are independently 0, 1, 2 or 3, provided both are not zero;

provided that when $R^{13}$ is —CH=CH— or —C($C_1$-$C_6$ alkyl)=CH—, a is 1;

provided that when $R^{14}$ is —CH=CH— or —C($C_1$-$C_6$ alkyl)=CH—, b is 1;

provided that when a is 2 or 3, the $R^{13}$'s can be the same or different; and provided that when b is 2 or 3, the $R^{14}$'s can be the same or different;

and when Q is a bond, $R^1$ also can be:

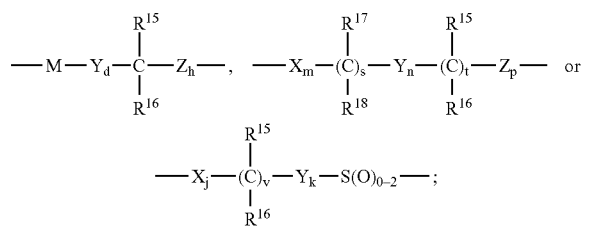

M is —O—, —S—, —S(O)— or —S(O)$_2$—;

X, Y and Z are independently selected from the group consisting of —CH$_2$—, —CH($C_1$-$C_6$)alkyl- and —C(di-($C_1$-$C_6$)alkyl);

$R^{10}$ and $R^{11}$ are independently selected from the group consisting of 1-3 substituents independently selected from the group consisting of ($C_1$-$C_6$)alkyl, —OR$^{19}$, —O(CO)R$^{19}$, —O(CO)OR$^{21}$, —O(CH$_2$)$_{1-5}$OR$^{19}$, —O(CO)NR$^{19}$R$^{20}$, —NR$^{19}$R$^{20}$, —NR$^{19}$(CO)R$^{20}$, —NR$^{19}$(CO)OR$^{21}$, —NR$^{19}$(CO)NR$^2$OR$^{25}$, —NR$^{19}$SO$_2$R$^{21}$, —COOR$^{19}$, —CONR$^{19}$R$^{20}$, —COR$^{19}$, —SO$_2$NR$^{19}$R$^{20}$, S(O)$_{0-2}$R$^{21}$, —O(CH$_2$)$_{1-10}$—COOR$^{19}$, —O(CH$_2$)$_{1-10}$CONR$^{19}$R$^{20}$, —($C_1$-$C_6$ alkylene)-COOR$^{19}$, —CH=CH—COOR$^{19}$, —CF$_3$, —CN, —NO$_2$ and halogen;

$R^{15}$ and $R^{17}$ are independently selected from the group consisting of —OR$^{19}$, —O(CO)R$^{19}$, —O(CO)OR$^{21}$ and —O(CO)NR$^{19}$R$^{20}$;

$R^{16}$ and $R^{18}$ are independently selected from the group consisting of H, ($C_1$-$C_6$)alkyl and aryl; or $R^{15}$ and $R^{16}$ together are =O, or $R^{17}$ and $R^{18}$ together are =O;

d is 1, 2 or 3;

h is 0, 1, 2, 3 or 4;

s is 0 or 1; t is 0 or 1; m, n and p are independently 0-4;

provided that at least one of s and t is 1, and the sum of m, n, p, s and t is 1-6;

provided that when p is 0 and t is 1, the sum of m, s and n is 1-5; and provided that when p is 0 and s is 1, the sum of m, t and n is 1-5;

v is 0 or 1;

j and k are independently 1-5, provided that the sum of j, k and v is 1-5;

and when Q is a bond and $R^1$ is

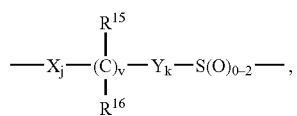

$Ar^1$ can also be pyridyl, isoxazolyl, furanyl, pyrrolyl, thienyl, imidazolyl, pyrazolyl, thiazolyl, pyrazinyl, pyrimidinyl or pyridazinyl;

$R^{19}$ and $R^{20}$ are independently selected from the group consisting of H, ($C_1$-$C_6$)alkyl, aryl and aryl-substituted ($C_1$-$C_6$)alkyl;

$R^{21}$ is ($C_1$-$C_6$)alkyl, aryl or $R^{24}$-substituted aryl;

$R^{22}$ is H, ($C_1$-$C_6$)alkyl, aryl($C_1$-$C_6$)alkyl, —C(O)R$^{19}$ or —COOR$^{19}$;

$R^{23}$ and $R^{24}$ are independently 1-3 groups independently selected from the group consisting of H, ($C_1$-$C_6$)alkyl, ($C_1$-$C_6$)alkoxy, —COOH, NO$_2$, —NR$^{19}$R$^{20}$, —OH and halogeno; and $R^{25}$ is H, —OH or ($C_1$-$C_6$)alkoxy.

Methods for making compounds of Formula VIII are well known to those skilled in the art. Non-limiting examples of suitable methods are disclosed in U.S. Pat. No. 5,756,470, which is incorporated herein by reference.

In another embodiment, sterol absorption inhibitors useful in the compositions and methods of the present invention are represented by Formula (IX) below:

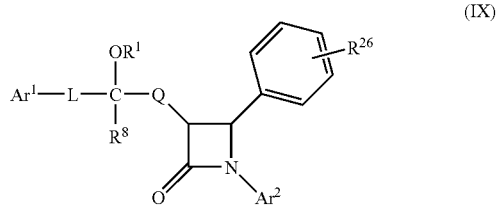

or a pharmaceutically acceptable salt or solvate thereof, wherein in Formula (IX):

$R^1$ is selected from the group consisting of H, G, G$^1$, G$^2$, —SO$_3$H and —PO$_3$H;

G is selected from the group consisting of: H,

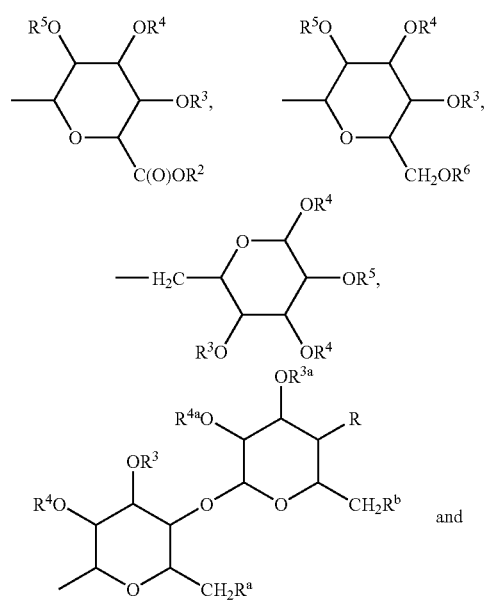

and

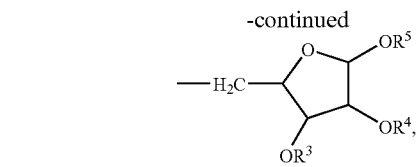

(sugar derivatives)

wherein R, $R^a$ and $R^b$ are each independently selected from the group consisting of H, —OH, halo, —$NH_2$, azido, ($C_1$-$C_6$)alkoxy($C_1$-$C_6$)alkoxy or —W—$R^{30}$;

W is independently selected from the group consisting of —NH—C(O)—, —O—C(O)—, —O—C(O)—N($R^{31}$)—, —NH—C(O)—N($R^{31}$)— and —O—C(S)—N($R^{31}$)—;

$R^2$ and $R^6$ are each independently selected from the group consisting of H, ($C_1$-$C_6$)alkyl, acetyl, aryl and aryl($C_1$-$C_6$)alkyl;

$R^3$, $R^4$, $R^5$, $R^7$, $R^{3a}$ and $R^{4a}$ are each independently selected from the group consisting of H, ($C_1$-$C_6$)alkyl, acetyl, aryl($C_1$-$C_6$)alkyl, —C(O)($C_1$-$C_6$)alkyl and C(O)aryl;

$R^{30}$ is independently selected from the group consisting of $R^{32}$-substituted T, $R^{32}$-substituted-T-($C_1$-$C_6$)alkyl, $R^{32}$-substituted-($C_2$-$C_4$)alkenyl, $R^{32}$-substituted-($C_1$-$C_6$)alkyl, $R^{32}$-substituted-($C_3$-$C_7$)cycloalkyl and $R^{32}$-substituted-($C_3$-$C_7$)cycloalkyl($C_1$-$C_6$)alkyl;

$R^{31}$ is independently selected from the group consisting of H and ($C_1$-$C_4$)alkyl;

T is independently selected from the group consisting of phenyl, furyl, thienyl, pyrrolyl, oxazolyl, isoxazolyl, thiazolyl, isothiazolyl, benzothiazolyl, thiadiazolyl, pyrazolyl, imidazolyl and pyridyl;

$R^{32}$ is independently selected from 1-3 substituents which are each independently selected from the group consisting of H, halo, ($C_1$-$C_4$)alkyl, —OH, phenoxy, —$CF_3$, —$NO_2$, ($C_1$-$C_4$)alkoxy, methylenedioxy, oxo, ($C_1$-$C_4$)alkylsulfanyl, ($C_1$-$C_4$)alkylsulfinyl, ($C_1$-$C_4$)alkylsulfonyl, —N($CH_3$)$_2$, —C(O)—NH($C_1$-$C_4$)alkyl, —C(O)—N(($C_1$-$C_4$)alkyl)$_2$, —C(O)—($C_1$-$C_4$)alkyl, —C(O)—($C_1$-$C_4$)alkoxy and pyrrolidinylcarbonyl; or $R^{32}$ is a covalent bond and $R^{31}$, the nitrogen to which it is attached and $R^{32}$ form a pyrrolidinyl, piperidinyl, N-methyl-piperazinyl, indolinyl or morpholinyl group, or a ($C_1$-$C_4$)alkoxycarbonyl-substituted pyrrolidinyl, piperidinyl, N-methylpiperazinyl, indolinyl or morpholinyl group;

$G^1$ is represented by the structure:

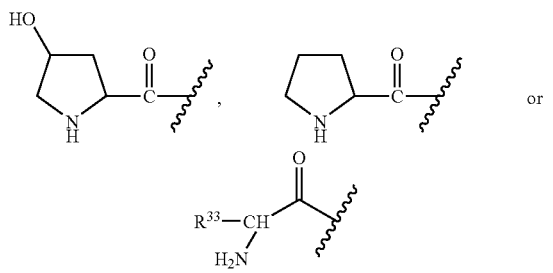

wherein $R^{33}$ is independently selected from the group consisting of unsubstituted alkyl, $R^{34}$-substituted alkyl, ($R^{35}$)($R^{36}$)alkyl-,

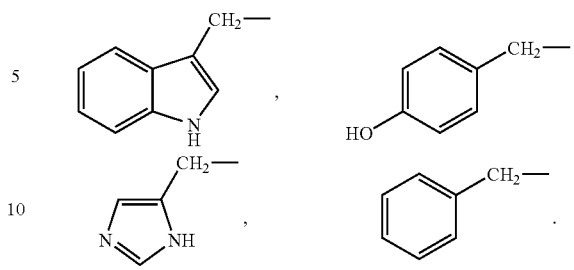

$R^{34}$ is one to three substituents, each $R^{34}$ being independently selected from the group consisting of HOOC—, HO—, HS—, ($CH_3$)S—, $H_2N$—, ($NH_2$)(NH)C(NH)—, ($NH_2$)C(O)— and HOOCCH($NH_3^+$)$CH_2$SS—;

$R^{35}$ is independently selected from the group consisting of H and $NH_2$—;

$R^{36}$ is independently selected from the group consisting of H, unsubstituted alkyl, $R^{34}$-substituted alkyl, unsubstituted cycloalkyl and $R^{34}$-substituted cycloalkyl;

$G^2$ is represented by the structure:

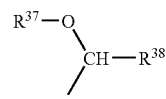

wherein $R^{37}$ and $R^{38}$ are each independently selected from the group consisting of ($C_1$-$C_6$)alkyl and aryl;

$R^{26}$ is one to five substituents, each $R^{26}$ being independently selected from the group consisting of:

a) H;
b) —OH;
c) —$OCH_3$;
d) fluorine;
e) chlorine;
f) —O-G;
g) —O-$G^1$;
h) —O-$G^2$;
i) —$SO_3H$; and
j) —$PO_3H$;

provided that when $R^1$ is H, $R^{26}$ is not H, —OH, —$OCH_3$ or —O-G;

$Ar^1$ is aryl, $R^{10}$-substituted aryl, heteroaryl or $R^{10}$-substituted heteroaryl;

$Ar^2$ is aryl, $R^{11}$-substituted aryl, heteroaryl or $R^{11}$-substituted heteroaryl;

L is selected from the group consisting of:

a) a covalent bond;
b) —($CH_2$)$_q$—, wherein q is 1-6;
c) —($CH_2$)$_e$-E-($CH_2$)$_r$—, wherein E is —O—, —C(O)—, phenylene, —$NR^{22}$— or —S(O)$_{0-2}$—, e is 0-5 and r is 0-5, provided that the sum of e and r is 1-6;
d) —($C_2$-$C_6$)alkenylene-;
e) —($CH_2$)$_f$—V—($CH_2$)$_g$—, wherein V is $C_3$-$C_6$cycloalkylene, f is 1-5 and g is 0-5, provided that the sum of f and g is 1-6; and f)

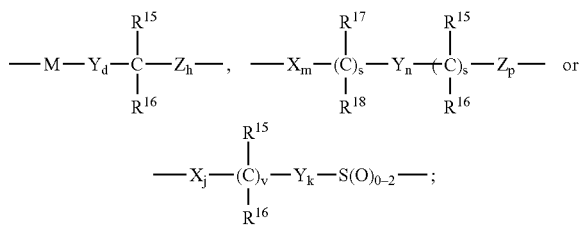

wherein M is —O—, —S—, —S(O)— or —S(O)$_2$—;

X, Y and Z are each independently selected from the group consisting of —CH$_2$—, —CH(C$_1$-C$_6$)alkyl- and —C(di-(C$_1$-C$_6$)alkyl)-;

R$^8$ is selected from the group consisting of H and alkyl;

R$^{10}$ and R$^{11}$ are each independently selected from the group consisting of 1-3 substituents which are each independently selected from the group consisting of (C$_1$-C$_6$)alkyl, —OR$^{19}$, —O(CO)R$^{19}$, —O(CO)OR$^{21}$, —O(CH$_2$)$_{1-5}$OR$^{19}$, —O(CO)NR$^{19}$R$^{20}$, —NR$^{19}$R$^{20}$, —NR$^{19}$(CO)R$^{20}$, —NR$^{19}$(CO)OR$^{21}$, —NR$^{19}$(CO)NR$^{20}$R$^{25}$, —NR$^{19}$SO$_2$R$^{21}$, —COOR$^{19}$, —CONR$^{19}$R$^{20}$, —COR$^{19}$, —SO$_2$NR$^{19}$R$^{20}$, S(O)$_{0-2}$R$^{21}$, —O(CH$_2$)$_{1-10}$—COOR$^{19}$, —O(CH$_2$)1-1 OCONR$^{19}$R$^{20}$, —(C$_1$-C$_6$ alkylene)-COOR$^{19}$, —CH=CH—COOR$^{19}$, —CF$_3$, —CN, —NO$_2$ and halo;

R$^{15}$ and R$^{17}$ are each independently selected from the group consisting of —OR$^{19}$, —OC(O)R$^{19}$, —OC(O)OR$^{21}$, —OC(O)NR$^{19}$R$^{20}$;

R$^{16}$ and R$^{18}$ are each independently selected from the group consisting of H, (C$_1$-C$_6$)alkyl and aryl;

or R$^{15}$ and R$^{16}$ together are =O, or R$^{17}$ and R$^{18}$ together are =O;

d is 1, 2 or 3;

h is 0, 1, 2, 3 or 4;

s is 0 or 1;

t is 0 or 1;

m, n and p are each independently selected from 0-4;

provided that at least one of s and t is 1, and the sum of m, n, p, s and t is 1-6; provided that when p is 0 and t is 1, the sum of m, n and p is 1-5; and provided that when p is 0 and s is 1, the sum of m, t and n is 1-5;

v is 0 or 1;

j and k are each independently 1-5, provided that the sum of j, k and v is 1-5;

Q is a bond, —(CH$_2$)$_q$—, wherein q is 1-6, or, with the 3-position ring carbon of the azetidinone, forms the spiro group

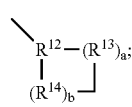

wherein R$^{12}$ is

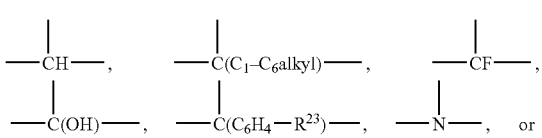

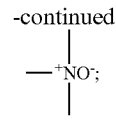

R$^{13}$ and R$^{14}$ are each independently selected from the group consisting of —CH$_2$—, —CH(C$_1$-C$_6$ alkyl)-, —C(di-(C$_1$-C$_6$)alkyl), —CH=CH— and —C(C$_1$-C$_6$ alkyl)=CH—; or R$^{12}$ together with an adjacent R$^{13}$, or R$^{12}$ together with an adjacent R$^{14}$, form a CH=CH— or a —CH=C(C$_1$-C$_6$ alkyl)- group;

a and b are each independently 0, 1, 2 or 3, provided both are not zero; provided that when R$^{13}$ is —CH=CH— or —C(C$_1$-C$_6$ alkyl)=CH—, a is 1; provided that when R$^{14}$ is —CH=CH— or —C(C$_1$-C$_6$ alkyl)=CH—, b is 1; provided that when a is 2 or 3, the R$^{13}$'s can be the same or different; and provided that when b is 2 or 3, the R$^{14}$'s can be the same or different;

and when Q is a bond and L is

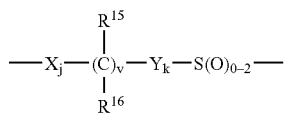

then Ar$^1$ can also be pyridyl, isoxazolyl, furanyl, pyrrolyl, thienyl, imidazolyl, pyrazolyl, thiazolyl, pyrazinyl, pyrimidinyl or pyridazinyl;

R$^{19}$ and R$^{20}$ are each independently selected from the group consisting of H, (C$_1$-C$_6$)alkyl, aryl and aryl-substituted (C$_1$-C$_6$)alkyl;

R$^{21}$ is (C$_1$-C$_6$)alkyl, aryl or R$^{24}$-substituted aryl;

R$^{22}$ is H, (C$_1$-C$_6$)alkyl, aryl(C$_1$-C$_6$)alkyl, —C(O)R$^{19}$ or —COOR$^{19}$;

R$^{23}$ and R$^{24}$ are each independently selected from the group consisting of 1-3 substituents which are each independently selected from the group consisting of H, (C$_1$-C$_6$)alkyl, (C$_1$-C$_6$)alkoxy, —COOH, NO$_2$, —NR$^{19}$R$^{20}$, —OH and halo; and R$^{25}$ is H, —OH or (C$_1$-C$_6$)alkoxy.

Examples of compounds of Formula (IX) which are useful in the methods and combinations of the present invention and methods for making such compounds are disclosed in U.S. patent application Ser. No. 10/166,942, filed Jun. 11, 2002, incorporated herein by reference.

An example of a useful compound of this invention is one represented by the formula X:

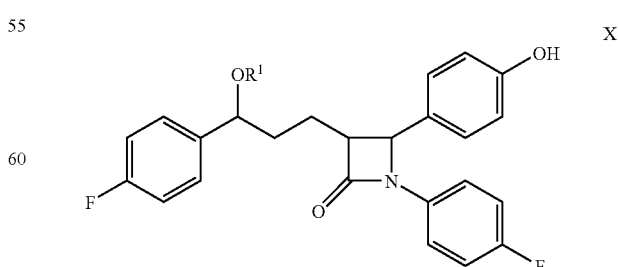

wherein R$^1$ is defined as above.

A more preferred compound is one represented by formula XI:

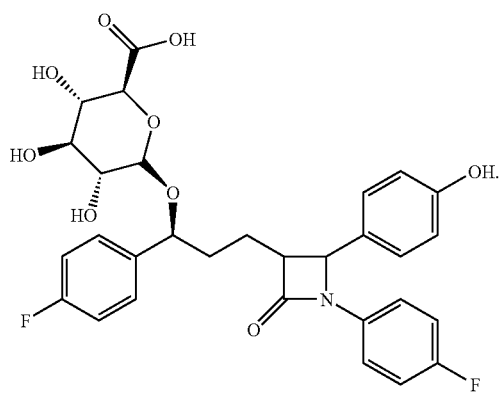

Another useful compound is represented by Formula XII:

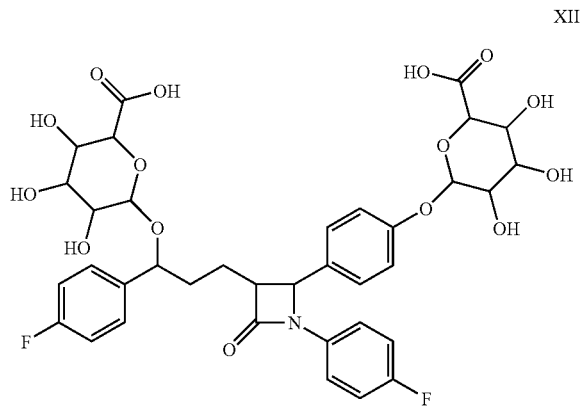

Other useful substituted azetidinone compounds include N-sulfonyl-2-azetidinones such as are disclosed in U.S. Pat. No. 4,983,597, ethyl 4-(2-oxoazetidin-4-yl)phenoxy-alkanoates such as are disclosed in Ram et al., Indian J. Chem. Sect. B. 29B, 12 (1990), p. 1134-7, and diphenyl azetidinones and derivatives disclosed in U.S. Patent Publication Nos. 2002/0039774, 2002/0128252, 2002/0128253 and 2002/0137689, and WO 2002/066464, each of which is incorporated by reference herein.

The compounds of Formulae I-XII can be prepared by known methods, including the methods discussed above and, for example, WO 93/02048 describes the preparation of compounds wherein —$R^1$-Q- is alkylene, alkenylene or alkylene interrupted by a hetero atom, phenylene or cycloalkylene; WO 94/17038 describes the preparation of compounds wherein Q is a spirocyclic group; WO 95/08532 describes the preparation of compounds wherein —$R^1$-Q- is a hydroxy-substituted alkylene group; PCT/US95/03196 describes compounds wherein —$R^1$-Q- is a hydroxy-substituted alkylene attached to the $Ar^1$ moiety through an —O— or $S(O)_{0-2}$- group; and U.S. Ser. No. 08/463,619, filed Jun. 5, 1995, describes the preparation of compounds wherein —$R^1$-Q- is a hydroxy-substituted alkylene group attached the azetidinone ring by a —$S(O)_{0-2}$- group.

Compounds of the invention have at least one asymmetrical carbon atom and therefore all isomers, including enantiomers, stereoisomers, rotamers, tautomers and racemates of the compounds of Formulae I-XII are contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of the Formulae I-XII. Isomers may also include geometric isomers, e.g., when a double bond is present.

Those skilled in the art will appreciate that for some of the compounds of the Formulas I-XII, one isomer will show greater pharmacological activity than other isomers.

Compounds of the invention with an amino group can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain compounds of the invention are acidic (e.g., those compounds which possess a carboxyl group). These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

As used herein, "solvate" means a molecular or ionic complex of molecules or ions of solvent with those of solute (for example, one or more compounds of Formulae I-XII, isomers of the compounds of Formulae I-XII, or prodrugs of the compounds of Formulae I-XII). Non-limiting examples of useful solvents include polar, protic solvents such as water and/or alcohols (for example methanol).

Prodrugs of the compounds of Formulae I-XII are contemplated as being part of this invention. As used herein, "prodrug" means compounds that are drug precursors which, following administration to a patient, release the drug in vivo via some chemical or physiological process (e.g., a prodrug on being brought to the physiological pH or through enzyme action is converted to the desired drug form).

The daily dose of the sterol absorption inhibitor(s) administered to the subject can range from about 0.1 to about 1000 mg per day, preferably about 0.25 to about 50 mg/day, and more preferably about 10 mg per day, given in a single dose or 2-4 divided doses. The exact dose, however, is determined by the attending clinician and is dependent on the potency of the compound administered, the age, weight, condition and response of the patient.

For administration of pharmaceutically acceptable salts of the above compounds, the weights indicated above refer to the weight of the acid equivalent or the base equivalent of the therapeutic compound derived from the salt.

The term "therapeutically effective amount" means that amount of a therapeutic agent of the composition, such as a sterol absorption inhibitor(s), antidemyelination agent and other pharmacological or therapeutic agents described below, that will elicit a biological or medical response of a tissue, system, or subject that is being sought by the administrator (such as a researcher, doctor or veterinarian) which includes alleviation of the symptoms of the condition or disease being treated and the prevention, slowing or halting of progression of the condition (demyelination and its symptom(s)).

Examples of suitable subjects that can be treated according to the methods of the present invention include mammals, such as humans or dogs, and other animals.

As used herein, "combination therapy" or "therapeutic combination" means the administration of two or more therapeutic agents, such as sterol absorption inhibitor(s) and antidemyelination agent(s), to prevent or treat demyelination or any of its associated conditions, such as are discussed above. As used herein, "demyelination" means insufficient or loss of myelin on the nerves. Such administration includes coadministration of these therapeutic agents in a substantially simultaneous manner, such as in a single tablet or capsule having a fixed ratio of active ingredients or in multiple, separate capsules for each therapeutic agent. Also, such administration includes use of each type of therapeutic agent in a sequential manner. In either case, the treatment using the combination therapy will provide beneficial effects in treating the demyelination condition. A potential advantage of the combination therapy disclosed herein may be a reduction in the required amount of an individual therapeutic compound or the overall total amount of therapeutic compounds that are effective in treating the demyelination condition. By using a combination of therapeutic agents, the side effects of the individual compounds can be reduced as compared to a monotherapy, which can improve patient compliance. Also, therapeutic agents can be selected to provide a broader range of complimentary effects or complimentary modes of action.

In another embodiment, the present invention provides a therapeutic combination comprising (a) a first amount of at least one sterol absorption inhibitor or a pharmaceutically acceptable salt thereof or a solvate thereof; and (b) a second amount of at least one antidemyelination agent or treatment, wherein the first amount and the second amount together comprise a therapeutically effective amount for the treatment or prevention of demyelination or lessening or amelioration of one or more symptoms of a condition associated with demyelination.

In another embodiment, the present invention provides a pharmaceutical composition for the treatment or prevention of diabetes and/or lowering a concentration of a sterol in plasma of a subject, comprising a therapeutically effective amount of a composition comprising (a) a first amount of at least one sterol absorption inhibitor or a pharmaceutically acceptable salt thereof or a solvate thereof; (b) a second amount of at least one antidemyelination agent and (c) a pharmaceutically acceptable carrier.

In another embodiment, the present invention provides a method of treating or preventing demyelination in a subject, comprising the step of administering to a subject in need of such treatment an effective amount of a composition comprising (a) a first amount of at least one sterol absorption inhibitor or a pharmaceutically acceptable salt thereof or a solvate thereof; and (b) a second amount of at least one antidemyelination agent to prevent or treat demyelination or any of its symptoms in the subject.

Useful antidemyelination agents include beta-interferon (such as AVONEX® which is available from Biogen, Inc. and BETASERON® which is available from Berlex Laboratories), which can decrease the frequency and occurrence of flare-ups and slow the progression to disability, glatiramer acetate (such as COPAXONE® which is available from Teva Neuroscience, Inc.), which can reduce the frequency of relapses, and/or administration of corticosteroids, such as prednisone (available from Roxane), to relieve acute symptoms. The amount of respective antidemyelination agent to be administered to the subject readily can be determined by one skilled in the art from the Physician's Desk Reference ($56^{th}$ Ed. 2002) at pages 1013-1016,988-995, 3306-3310 and 3064-3066, incorporated herein by reference.

Also useful with the present invention are compositions or therapeutic combinations that can further comprise one or more pharmacological or therapeutic agents or drugs such as cholesterol biosynthesis inhibitors and/or lipid-lowering agents discussed below.

Non-limiting examples of cholesterol biosynthesis inhibitors for use in the compositions, therapeutic combinations and methods of the present invention include competitive inhibitors of HMG CoA reductase, the rate-limiting step in cholesterol biosynthesis, squalene synthase inhibitors, squalene epoxidase inhibitors and mixtures thereof. Non-limiting examples of suitable HMG CoA reductase inhibitors include statins such as atorvastatin (for example LIPITOR® which is available from Pfizer), lovastatin (for example MEVACOR® which is available from Merck & Co.), pravastatin (for example PRAVACHOL® which is available from Bristol Meyers Squibb), fluvastatin, simvastatin (for example ZOCOR® which is available from Merck & Co.), cerivastatin, CI-981, rivastatin (sodium 7-(4-fluorophenyl)-2,6-diisopropyl-5-methoxymethylpyridin-3-yl)-3,5-dihydroxy-6-heptanoate) and pitavastatin (such as NK104 of Negma Kowa of Japan). Preferred HMG CoA reductase inhibitors include atorvastatin and simvastatin. Generally, a total daily dosage of cholesterol biosynthesis inhibitor(s) can range from about 0.1 to about 160 mg per day, and preferably about 0.2 to about 80 mg/day in single or 2-3 divided doses.

Also useful with the present invention are compositions or therapeutic combinations that can further comprise at least one (one or more) activators for peroxisome proliferator-activated receptors (PPAR), such as peroxisome proliferator-activated receptor alpha (PPARα), peroxisome proliferator-activated receptor gamma (PPARγ) and peroxisome proliferator-activated receptor delta (PPARδ). PPARα activator compounds are useful for, among other things, lowering triglycerides, moderately lowering LDL levels and increasing HDL levels. Useful examples of PPARα activators include fibrates, such as clofibrate, gemfibrozil and fenofibrate. The PPAR activator(s) are administered in a therapeutically effective amount to treat the specified condition, for example in a daily dose preferably ranging from about 50 to about 3000 mg per day.

The compositions, therapeutic combinations or methods of the present invention can further comprise one or more bile acid sequestrants such as cholestyramine, colestipol and colesevelam hydrochloride. Generally, a total daily dosage of bile acid sequestrant(s) can range from about 1 to about 50 grams per day, and preferably about 2 to about 16 grams per day in single or 2-4 divided doses.

The compositions or treatments of the present invention can further comprise one or more ileal bile acid transport ("IBAT") inhibitors (or apical sodium co-dependent bile acid transport ("ASBT") inhibitors) coadministered with or in combination with the peroxisome proliferator-activated receptor activator(s) and sterol absorption inhibitor(s) discussed above. The IBAT inhibitors can inhibit bile acid transport to reduce LDL cholesterol levels. Non-limiting examples of suitable IBAT inhibitors include benzothiepines such as are disclosed in PCT Patent Application WO 00/38727 which is incorporated herein by reference. Generally, a total daily dosage of IBAT inhibitor(s) can range from about 0.01 to about 1000 mg/day, and preferably about 0.1 to about 50 mg/day in single or 2-4 divided doses.

The compositions or treatments of the present invention can further comprise nicotinic acid (niacin) and/or derivatives thereof, such as NIASPAN® (niacin extended release tablets) which are available from Kos. Generally, a total daily dosage of nicotinic acid or a derivative thereof can range from about 500 to about 10,000 mg/day, preferably about 1000 to about 8000 mg/day, and more preferably about 3000 to about 6000 mg/day in single or divided doses.

The compositions or treatments of the present invention can further comprise one or more AcylCoA:Cholesterol O-acyltransferase ("ACAT") Inhibitors, which can reduce LDL and VLDL levels. Non-limiting examples of useful ACAT inhibitors include avasimibe. Generally, a total daily dosage of ACAT inhibitor(s) can range from about 0.1 to about 1000 mg/day in single or 2-4 divided doses.

The compositions or treatments of the present invention can further comprise one or more Cholesteryl Ester Transfer Protein ("CETP") Inhibitors. CETP is responsible for the exchange or transfer of cholesteryl ester carrying HDL and triglycerides in VLDL. Non-limiting examples of suitable CETP inhibitors are disclosed in PCT Patent Application No. WO 00/38721 and U.S. Pat. No. 6,147,090, which are incorporated herein by reference. Generally, a total daily dosage of CETP inhibitor(s) can range from about 0.01 to about 1000 mg/day, and preferably about 0.5 to about 20 mg/kg body weight/day in single or divided doses.

The compositions or treatments of the present invention can further comprise probucol or derivatives thereof, which can reduce LDL levels. Generally, a total daily dosage of probucol or derivatives thereof can range from about 10 to about 2000 mg/day, and preferably about 500 to about 1500 mg/day in single or 2-4 divided doses.

The compositions or treatments of the present invention can further comprise low-density lipoprotein (LDL) receptor activators such as HOE-402, an imidazolidinyl-pyrimidine derivative that directly stimulates LDL receptor activity. Generally, a total daily dosage of LDL receptor activator(s) can range from about 1 to about 1000 mg/day in single or 2-4 divided doses.

The compositions or treatments of the present invention can further comprise fish oil, which contains Omega 3 fatty acids (3-PUFA), which can reduce VLDL and triglyceride levels. Generally, a total daily dosage of fish oil or Omega 3 fatty acids can range from about 1 to about 30 grams per day in single or 2-4 divided doses.

The compositions or treatments of the present invention can further comprise natural water soluble fibers, such as psyllium, guar, oat and pectin, which can reduce cholesterol levels. Generally, a total daily dosage of natural water soluble fibers can range from about 0.1 to about 10 grams per day in single or 2-4 divided doses.

The compositions or treatments of the present invention can further comprise plant sterols, plant stanols and/or fatty acid esters of plant stanols, such as sitostanol ester used in BENECOL® margarine, which can reduce cholesterol levels. Generally, a total daily dosage of plant sterols, plant stanols and/or fatty acid esters of plant stanols can range from about 0.5 to about 20 grams per day in single or 2-4 divided doses.

The compositions or treatments of the present invention can further comprise antioxidants, such as probucol, tocopherol, ascorbic acid, β-carotene and selenium, or vitamins such as vitamin $B_6$ or vitamin $B_{12}$. Generally, a total daily dosage of antioxidants or vitamins can range from about 0.05 to about 10 grams per day in single or 2-4 divided doses.

The compositions or treatments of the present invention can further comprise monocyte and macrophage inhibitors such as polyunsaturated fatty acids, gene therapy and use of recombinant proteins such as recombinant apo E. Generally, a total daily dosage of these agents can range from about 0.01 to about 1000 mg/day in single or 2-4 divided doses.

The compositions, therapeutic combinations or methods of the present invention can further comprise one or more cardiovascular agents or blood modifiers.

Mixtures of any of the pharmacological or therapeutic agents described above can be used in the compositions and therapeutic combinations of these other embodiments of the present invention.

The compositions and therapeutic combinations of the present invention can be administered to a subject in need of such treatment in a therapeutically effective amount to treat demyelination and its associated conditions as discussed above. The compositions and treatments can be administered by any suitable means which produce contact of these compounds with the site of action in the body, for example in the plasma, liver or small intestine of a subject.

The daily dosage for the various compositions and therapeutic combinations described above can be administered to a subject in a single dose or in multiple subdoses, as desired. Subdoses can be administered 2 to 6 times per day, for example. Sustained release dosages can be used. Where the antidemyelination agent and sterol absorption inhibitor(s) are administered in separate dosages, the number of doses of each component given per day may not necessarily be the same, e.g., one component may have a greater duration of activity and will therefore need to be administered less frequently.

The compositions, therapeutic combinations or medicaments of the present invention can further comprise one or more pharmaceutically acceptable carriers, one or more excipients and/or one or more additives. The pharmaceutical compositions can comprise about 1 to about 99 weight percent of active ingredient (such as one or more compounds of Formula I-XII), and preferably about 5 to about 95 percent active ingredient.

Useful pharmaceutically acceptable carriers can be either solid, liquid or gas. Non-limiting examples of pharmaceutically acceptable carriers include solids and/or liquids such as magnesium carbonate, magnesium stearate, talc, sugar, lactose, ethanol, glycerol, water and the like. The amount of carrier in the treatment composition or therapeutic combination can range from about 5 to about 99 weight percent of the total weight of the treatment composition or therapeutic combination. Non-limiting examples of suitable pharmaceutically acceptable excipients and additives include non-toxic compatible fillers, binders such as starch, polyvinyl pyrrolidone or cellulose ethers, disintegrants such as sodium starch glycolate, crosslinked polyvinyl pyrrolidone or croscarmellose sodium, buffers, preservatives, anti-oxidants, lubricants, flavorings, thickeners, coloring agents, wetting agents such as sodium lauryl sulfate, emulsifiers and the like. The amount of excipient or additive can range from about 0.1 to about 95 weight percent of the total weight of the treatment composition or therapeutic combination. One skilled in the art would understand that the amount of carrier(s), excipients and additives (if present) can vary. Further examples of pharmaceutically acceptable carriers and methods of manufacture for various compositions can be found in A. Gennaro (ed.), Remington: The Science and Practice of Pharmacy, 20th Edition, (2000), Lippincott Williams & Wilkins, Baltimore, Md.

Useful solid form preparations include powders, tablets, dispersible granules, capsules, cachets and suppositories. An example of a preparation of a preferred solid form dosage formulation is provided below.

Useful liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also useful are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

In another embodiment, the present invention provides the use of at least one compound represented by Formulae (I-XII) for manufacture of a medicament (such as one of the compositions discussed above) for the treatment of demyelination and its associated conditions.

The following formulation exemplifies one of the dosage forms of this invention. In the formulation, the term "Active Compound I" designates a sterol absorption inhibitor such as any of the compounds of Formulas I-XII described herein above and the term "Active Compound II" designates an antidemyelination agent described herein above.

EXAMPLE

Tablets

| No. | Ingredient | mg/tablet |
|---|---|---|
| 1 | Active Compound I | 10 |
| 2 | Lactose monohydrate NF | 55 |
| 3 | Microcrystalline cellulose NF | 20 |
| 4 | Povidone USP (K29-32) | 4 |
| 5 | Croscarmellose sodium NF | 8 |
| 6 | Sodium lauryl sulfate NF | 2 |
| 7 | Magnesium stearate NF | 1 |
| | Total | 100 |

In the present invention, the above-described tablet can be coadministered with an injection, tablet, capsule, etc. comprising a dosage of Active Compound II as described above.

Method of Manufacture

Mix Item No. 4 with purified water in suitable mixer to form binder solution. Spray the binder solution and then water over Items 1, 2 and 6 and a portion of item 5 in a fluidized bed processor to granulate the ingredients. Continue fluidization to dry the damp granules. Screen the dried granule and blend with Item No. 3 and the remainder of Item No. 5. Add Item No. 7 and mix. Compress the mixture to appropriate size and weight on a suitable tablet machine.

For coadministration in separate tablets or capsules, representative formulations comprising a sterol absorption inhibitor such as discussed above are well known in the art and representative formulations comprising an antidemyelination agent such as are discussed above are well known in the art. It is contemplated that where the two active ingredients are administered as a single composition, the dosage forms disclosed above for sterol absorption inhibitors may readily be modified using the knowledge of one skilled in the art.

Since the present invention relates to treating demyelination by treatment with a combination of active ingredients wherein the active ingredients may be administered separately, the invention also relates to combining separate pharmaceutical compositions in kit form. That is, a kit is contemplated wherein two separate units are combined: a pharmaceutical composition comprising at least one antidemyelination medication and a separate pharmaceutical composition comprising at least one sterol absorption inhibitor as described above. The kit will preferably include directions for the administration of the separate components. The kit form is particularly advantageous when the separate components must be administered in different dosage forms (e.g., oral and parenteral) or are administered at different dosage intervals.

The treatment compositions and therapeutic combinations of the present invention can inhibit the intestinal absorption of sterols in subjects and can be useful in the treatment and/or prevention of demyelination and associated conditions, such as multiple sclerosis, in subjects, in particular in mammals.

The compositions and therapeutic combinations of the present invention can reduce plasma concentration of at least one sterol selected from the group consisting of cholesterol, phytosterols (such as sitosterol, campesterol, stigmasterol and avenosterol), and/or 5α-stanols (such as cholestanol, 5α-campestanol, 5α-sitostanol), and mixtures thereof. The plasma concentration can be reduced by administering to a subject in need of such treatment an effective amount of at least one treatment composition comprising at least one sterol or 5α-stanol absorption inhibitor described above. The reduction in plasma concentration of sterols or 5α-stanols can range from about 1 to about 70 percent, and preferably about 10 to about 50 percent. Methods of measuring serum total blood cholesterol and total LDL cholesterol are well known to those skilled in the art and for example include those disclosed in PCT WO 99/38498 at page 11, incorporated by reference herein. Methods of determining levels of other sterols in serum are disclosed in H. Gylling et al., "Serum Sterols During Stanol Ester Feeding in a Mildly Hypercholesterolemic Population", J. Lipid Res. 40: 593-600 (1999), incorporated by reference herein.

These sterol absorption inhibitors can be useful in treating or preventing vascular inflammation. Vascular stimuli to mammals, such as cellular injury or inflammation, may lead to the production of various proteins, commonly called acute response proteins, in the body. One particular type of acute phase protein is C-reactive protein (CRP). Manufactured in the liver and deposited in damaged tissue, CRP is found in high levels in inflammatory fluids and in both the intimal layer of the atherosclerotic artery and within the lesions of atherosclerotic plaque. These sterol absorption inhibitors can be useful for lowering or controlling c-reactive protein blood levels in a subject to less than about 3.4 mg/dL. Preferably, the C-reactive protein blood levels in a subject are reduced or controlled to less than 1.0 mg/dL by the methods of the present invention. More preferably, the C-reactive protein blood levels in a subject are reduced or controlled to less than 0.4 mg/dL by the methods of the present invention. C-reactive protein assays and methodologies for the same are available from Behring Diagnostics Inc., of Somerville, N.J. Moreover, methods for analyzing c-reactive proteins are described in U.S. Pat. Nos. 5,358,852; 6,040,147; and 6,277,584, whose contents are incorporated herein by reference.

Illustrating the invention is the following example of preparation of a compound of Formula II which, however, is not to be considered as limiting the invention to their details. Unless otherwise indicated, all parts and percentages in the following examples, as well as throughout the specification, are by weight.

Example

Preparation of Compound of Formula (II)

Step 1): To a solution of (S)-4-phenyl-2-oxazolidinone (41 g, 0.25 mol) in $CH_2Cl_2$ (200 ml), was added 4-dimethylaminopyridine (2.5 g, 0.02 mol) and triethylamine (84.7 ml, 0.61 mol) and the reaction mixture was cooled to OOC. Methyl-4-(chloroformyl)butyrate (50 g, 0.3 mol) was added as a solution in $CH_2Cl_2$ (375 ml) dropwise over 1 h, and the reaction was allowed to warm to 22° C. After 17 h, water and $H_2SO_4$ (2N, 100 ml), was added the layers were separated, and the organic layer was washed sequentially with NaOH (10%), NaCl (sat'd) and water. The organic layer was dried over $MgSO_4$ and concentrated to obtain a semicrystalline product.

Step 2): To a solution of $TiCl_4$ (18.2 ml, 0.165 mol) in $CH_2$-$Cl_2$ (600 ml) at 0° C., was added titanium isopropoxide (16.5 ml, 0.055 mol). After 15 min, the product of Step 1 (49.0 g, 0.17 mol) was added as a solution in $CH_2Cl_2$ (100 ml). After 5 min., diisopropylethylamine (DIPEA) (65.2 ml, 0.37 mol) was added and the reaction mixture was stirred at OOC for 1 h, the reaction mixture was cooled to −20° C., and 4-benzyloxybenzylidine(4-fluoro)aniline (114.3 g, 0.37 mol) was added as a solid. The reaction mixture was stirred vigorously for 4 h at −20° C., then acetic acid was added as a solution in $CH_2Cl_2$ dropwise over 15 min, the reaction mixture was allowed to warm to 0° C., and $H_2SO_4$ (2N) was added. The reaction mixture was stirred an additional 1 h, the layers were separated, washed with water, separated and the organic layer was dried. The crude product was crystallized from ethanol/water to obtain the pure intermediate.

Step 3): To a solution of the product of Step 2 (8.9 g, 14.9 mmol) in toluene (100 ml) at 50° C., was added N,O-bis(trimethylsilyl)acetamide (BSA) (7.50 ml, 30.3 mmol). After 0.5 h, solid TBAF (0.39 g, 1.5 mmol) was added and the reaction mixture stirred at 50° C. for an additional 3 h. The reaction mixture was cooled to 22° C., $CH_3OH$ (10 ml), was added. The reaction mixture was washed with HCl (1N), $NaHCO_3$ (1N) and NaCl (sat'd.), and the organic layer was dried over $MgSO_4$.

Step 4): To a solution of the product of Step 3 (0.94 g, 2.2 mmol) in $CH_3OH$ (3 ml), was added water (1 ml) and $LiOH.H_2O$ (102 mg, 2.4 mmole). The reaction mixture was stirred at 22° C. for 1 h and then additional $LiOH.H_2O$ (54 mg, 1.3 mmole) was added. After a total of 2 h, HCl (1 N) and EtOAc was added, the layers were separated, the organic layer was dried and concentrated in vacuo. To a solution of the resultant product (0.91 g, 2.2 mmol) in $CH_2Cl_2$ at 22° C., was added ClCOCOCl (0.29 ml, 3.3 mmol) and the mixture stirred for 16 h. The solvent was removed in vacuo.

Step 5): To an efficiently stirred suspension of 4-fluorophenylzinc chloride (4.4 mmol) prepared from 4-fluorophenyl-magnesium bromide (1 M in THF, 4.4 ml, 4.4 mmol) and $ZnCl_2$ (0.6 g, 4.4 mmol) at 4° C., was added tetrakis(triphenyl-phosphine)palladium (0.25 g, 0.21 mmol) followed by the product of Step 4 (0.94 g, 2.2 mmol) as a solution in THF (2 ml). The reaction was stirred for 1 h at 0° C. and then for 0.5 h at 22° C. HCl (1 N, 5 ml) was added and the mixture was extracted with EtOAc. The organic layer was concentrated to an oil and purified by silica gel chromatography to obtain 1-(4-fluorophenyl)-4(S)-(4-hydroxyphenyl)-3(R)-(3-oxo-3-phenylpropyl)-2-azetidinone:

HRMS calc'd for $C_{24}H_{19}F_2NO_{3=408.1429}$, found 408.1411.

Step 6): To the product of Step 5 (0.95 g, 1.91 mmol) in THF (3 ml), was added (R)-tetrahydro-1-methyl-3,3-diphenyl-1H,3H-pyrrolo-[1,2-c][1,3,2]oxazaborole (120 mg, 0.43 mmol) and the mixture was cooled to −20° C. After 5 min, borohydride-dimethylsulfide complex (2M in THF, 0.85 ml, 1.7 mmol) was added dropwise over 0.5 h. After a total of 1.5 h, $CH_3OH$ was added followed by HCl (1 N) and the reaction mixture was extracted with EtOAc to obtain 1-(4-fluorophenyl)-3(R)-[3(S)-(4-fluorophenyl)-3-hydroxypropyl)]4(S)-[4-(phenylmethoxy)phenyl]-2-azetidinone (compound 6A-1) as an oil. $^1H$ in $CDCl_3$ d $H_{3=4.68}$. J=2.3 Hz. Cl (M+H) 500.

Use of (S)-tetra-hydro-1-methyl-3,3-diphenyl-1H,3H-pyrrolo-[1,2-c][1,3,2] oxazaborole gives the corresponding 3(R)-hydroxypropyl azetidinone (compound 6B-1). $^1H$ in $CDCl_3$ d H3=4.69. J=2.3 Hz. Cl (M+H) 500.

To a solution of compound 6A-1 (0.4 g, 0.8 mmol) in ethanol (2 ml), was added 10% Pd/C (0.03 g) and the reaction mixture was stirred under a pressure (60 psi) of $H_2$ gas for 16 h. The reaction mixture was filtered and the solvent was concentrated to obtain compound 6A. Mp 164-166° C.; Cl (M+H) 410. $[\alpha]_D^5 = -28.1°$ (c 3, $CH_3OH$).

Elemental analysis calc'd for $C_{24}H_{21}F_2NO_3$: C,70.41; H,5.17; N,3.42; found C,70.25; H,5.19; N,3.54.

Similarly treat compound 6B-1 to obtain compound 6B.

Mp 129.5-132.5° C.; Cl (M+H) 410. Elemental analysis calc'd for $C_{24}H_{21}F_2NO_3$: C,70.41; H,5.17; N, 3.42; found C,70.30; H,5.14; N,3.52.

Step 6' (Alternative): To a solution of the product of Step 5 (0.14 g, 0.3 mmol) in ethanol (2 ml), was added 10% Pd/C (0.03 g) and the reaction was stirred under a pressure (60 psi) of $H_2$ gas for 16 h. The reaction mixture was filtered and the solvent was concentrated to afford a 1:1 mixture of compounds 6A and 6B.

Hypothetical In Vivo Evaluation

The compound of Formula II (or any cholesterol absorption inhibitor discussed above) is administered to rodents which have been induced to develop experimental autoimmune encephalomyelitis ("EAE"), a model of human multiple sclerosis and demyelinating disease. Useful rodents can include C57BL/6 mice (obtained from the Jackson Laboratory or Charles River Laboratories) immunized with myelin oligodendrocyte protein (MOG) 35-55 peptide, SJL/J (also available from Jackson Laboratory or Charles River Laboratories) mice immunized with proteolipid protein (PLP) peptides, or Lewis, BN or DA rats (obtained from Charles River Laboratories or Harlan Laboratories) immunized with guinea pig spinal cord homogenate or myelin basic protein (MBP). All immunizations are performed by emulsifying the inducing peptide in either incomplete Freund's adjuvant or complete Freund's adjuvant, with or without pertussis toxin administration (as described in *Current Protocols in Immunology*, Unit 15, John Wiley & Sons, Inc. NY, or Tran et al, *Eur. J. Immunol.* 30:1410, 2002 or H. Butzkeuven et al, *Nat. Med.* 8:613, 2002).

Alternatively, the compound of Formula II (or any cholesterol absorption inhibitor discussed above) is administered to anti-MBP T cell receptor transgenic mice (as in Grewal et al *Immunity* 14:291, 2001), which naturally develop EAE disease.

Alternatively the compound of Formula II (or any cholesterol absorption inhibitor discussed above) is administered to rodents adoptively transferred with MBP-specific, PLP-specific or MOG-specific T cell lines (as described in *Current Protocols in Immunology*, Unit 15, John Wiley & Sons, Inc. NY).

Alternatively, the compound of Formula II (or any cholesterol absorption inhibitor discussed above) is administered to SJL/J or C57BL/6 mice which can be induced to develop a profound demyelinating disease by intracerebral inoculation with Theiler's murine encephalomyelitis virus (as described in Pope et al, *J. Immunol.* 156:4050, 1994) or by intraperitoneal injection of Simliki Forest virus (as described in Soilu-Hanninen et al, *J. Virol.* 68:6291, 1994).

The compound is administered at a dosage of 0.1-50 mg/kg/day either in the diet or by systemic oral, subcutaneous or intraperitoneal administration over a period of 4-10 weeks. Animals are scored daily for clinical disease score as described in *Current Protocols in Immunology*, Unit 15, John Wiley & Sons, Inc. NY, or Tran et al, *Eur. J. Immunol.* 30:1410, 2002 or H. Butzkeuven et al, *Nat. Med.* 8:613, 2002). At a specified period of compound administration, animals are euthanized by $CO_2$ asphyxiation and histological, immunohistochemical and immunological parameters measured as in Tran et al, *Eur. J. Immunol.* 30:1410, 2002 or H. Butzkeuven et al, *Nat. Med.* 8:613, 2002. Serum lipoprotein and cholesterol measurements will be made by standard techniques well known to those skilled in the art.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

The invention claimed is:

1. A method of treating demyelination in a subject, comprising the step of administering to a subject in need of such treatment an effective amount of at least one sterol absorption inhibitor or a pharmaceutically acceptable salt or solvate thereof, wherein the at least one sterol absorption inhibitor is:

Formula (I):

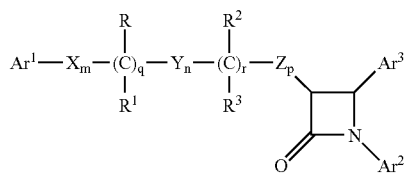

or a pharmaceutically acceptable salt thereof or a solvate thereof,
wherein:
Ar$^1$ and Ar$^2$ are independently selected from the group consisting of aryl and R$^4$-substituted aryl;
Ar$^3$ is aryl or R$^5$-substituted aryl;
X, Y and Z are independently selected from the group consisting of —CH$_2$—, —CH(lower alkyl)- and —C(dilower alkyl)-;
R and R$^2$ are independently selected from the group consisting of —OR$^6$, —O(CO)R$^6$, —O(CO)OR$^9$ and —O(CO)NR$^6$R$^7$;
R$^1$ and R$^3$ are independently selected from the group consisting of hydrogen, lower alkyl and aryl;
q is 0 or 1;
r is 0 or 1;
m, n and p are independently selected from 0, 1, 2, 3 or 4; provided that at least one of q and r is 1, and the sum of m, n, p, q and r is 1, 2, 3, 4, 5 or 6; and provided that when p is 0 and r is 1, the sum of m, q and n is 1, 2, 3, 4 or 5;
R$^4$ is 1-5 substituents independently selected from the group consisting of lower alkyl, —OR$^6$, —O(CO)R$^6$, —O(CO)OR$^9$, —O(CH$_2$)$_{1-5}$OR$^6$, —O(CO)NR$^6$R$^7$, —NR$^6$R$^7$, —NR$^6$(CO)R$^7$, —NR$^6$(CO)OR$^9$, —NR$^6$(CO)NR$^7$R$^8$, —NR$^6$SO$_2$R$^9$, —COOR$^6$, —CONR$^6$R$^7$, —COR$^6$, —SO$_2$NR$^6$R$^7$, S(O)$_{0-2}$R$^9$, —O(CH$_2$)$_{1-10}$—COOR$^6$, —O(CH$_2$)$_{1-10}$CONR$^6$R$^7$, -(lower alkylene)COOR$^6$, —CH═CH—COOR$^6$, —CF$_3$, —CN, —NO$_2$ and halogen;
R$^5$ is 1-5 substituents independently selected from the group consisting of —OR$^6$, —O(CO)R$^6$, —O(CO)OR$^9$, —O(CH$_2$)$_{1-5}$OR$^6$, —O(CO)NR$^6$R$^7$, —NR$^6$R$^7$, —NR$^6$(CO)R$^7$, —NR$^6$(CO)OR$^9$, —NR$^6$(CO)NR$^7$R$^8$, —NR$^6$SO$_2$R$^9$, —COOR$^6$, —CONR$^6$R$^7$, —COR$^6$, —SO$_2$NR$^6$R$^7$, S(O)$_{0-2}$R$^9$, —O(CH$_2$)$_{1-10}$—COOR$^6$, —O(CH$_2$)$_{1-10}$CONR$^6$R$^7$, -(lower alkylene)COOR$^6$ and —CH═CH—COOR$^6$;
R$^6$, R$^7$ and R$^8$ are independently selected from the group consisting of hydrogen, lower alkyl, aryl and aryl-substituted lower alkyl; and
R$^9$ is lower alkyl, aryl or aryl-substituted lower alkyl.

2. The method according to claim 1, wherein the at least one sterol absorption inhibitor is represented by Formula (I):

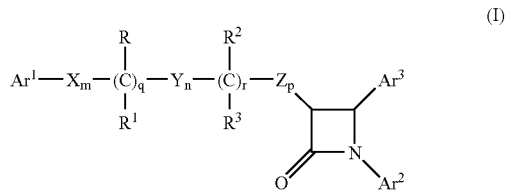

or a pharmaceutically acceptable salt thereof or a solvate thereof,
wherein:
Ar$^1$ and Ar$^2$ are independently selected from the group consisting of aryl and R$^4$-substituted aryl;
Ar$^3$ is aryl or R$^5$-substituted aryl;
X, Y and Z are independently selected from the group consisting of —C$_2$—, —CH(lower alkyl)- and —C(dilower alkyl)-;
R and R$^2$ are independently selected from the group consisting of —OR$^6$, —O(CO)R$^6$, —O(CO)OR$^9$ and —O(CO)NR$^6$R$^7$;
R$^1$ and R$^3$ are independently selected from the group consisting of hydrogen, lower alkyl and aryl;
q is 0 or 1;
r is 0 or 1;
m, n and p are independently selected from 0, 1, 2, 3 or 4; provided that at least one of q and r is 1, and the sum of m, n, p, q and r is 1, 2, 3, 4, 5 or 6; and provided that when p is 0 and r is 1, the sum of m, q and n is 1, 2, 3, 4 or 5;
R$^4$ is 1-5 substituents independently selected from the group consisting of lower alkyl, —OR$^6$, —O(CO)R$^6$, —O(CO)OR$^9$, —O(CH$_2$)$_{1-5}$OR$^6$, —O(CO)NR$^6$R$^7$, —NR$^6$R$^7$, —NR$^6$(CO)R$^7$, —NR$^6$(CO)OR$^9$, —NR$^6$(CO)NR$^7$R$^8$, —NR$^6$SO$_2$R$^9$, —COOR$^6$, —CONR$^6$R$^7$, —COR$^6$, —SO$_2$NR$^6$R$^7$, S(O)$_{0-2}$R$^9$, —O(CH$_2$)$_{1-10}$—

COOR⁶, —O(CH₂)₁₋₁₀CONRR⁶R⁷, -(lower alkylene)COOR⁶, —CH=CH—COOR⁶, —CF₃, —CN, —NO₂ and halogen;

R⁵ is 1-5 substituents independently selected from the group consisting of —OR⁶, —O(CO)R⁶, —O(CO)OR⁹, —O(CH₂)₁₋₅OR⁶, —O(CO)NR⁶R⁷, —NR⁶R⁷, —NR⁶(CO)R⁷, —NR⁶(CO)OR⁹, —NR⁶(CO)NR⁷R⁸, —NR⁶SO₂R⁹, —COOR⁶, —CONR⁶R⁷, —COR⁶, —SO₂NR⁶R⁷, S(O)₀₋₂R⁹, —O(CH₂)₁₋₁₀—COOR⁶, —O(CH₂)₁₋₁₀CONR⁶R⁷, -(lower alkylene)COOR⁶ and —CH=CH—COOR⁶;

R⁶, R⁷ and R⁸ are independently selected from the group consisting of hydrogen, lower alkyl, aryl and aryl-substituted lower alkyl; and R⁹ is lower alkyl, aryl or aryl-substituted lower alkyl.

3. The method according to claim 1, wherein the at least one sterol absorption inhibitor is administered to a subject in an amount ranging from about 0.1 to about 1000 milligrams of sterol absorption inhibitor per day.

4. The method according to claim 1, further comprising the step of administering at least one antidemyelination agent to the subject.

5. The method according to claim 4, wherein the antidemyelination agent is selected from the group consisting of beta interferon, glatiramer acetate and corticosteroids.

6. The method according to claim 1, further comprising the step of administering at least one HMG CoA reductase inhibitor to the subject.

7. The method according to claim 6, wherein the at least one HMG CoA reductase inhibitor is atorvastatin.

8. The method according to claim 6, wherein the at least one HMG CoA reductase inhibitor is simvastatin.

9. The method according to claim 1, wherein the subject has multiple sclerosis.

10. A method of treating demyelination in a subject is provided, comprising the step of administering to a subject in need of such treatment an effective amount of at least one sterol absorption inhibitor represented by Formula (II) below:

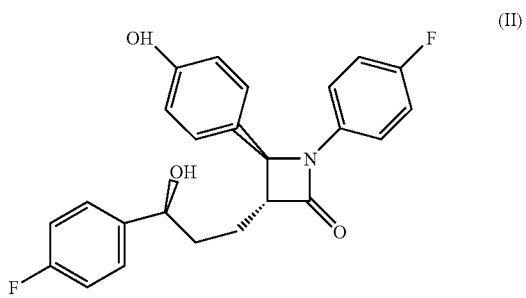

(II)

or a pharmaceutically acceptable salt or solvate thereof.

11. A method of treating multiple sclerosis in a subject, comprising the step of administering to a subject in need of such treatment an effective amount of at least one sterol absorption inhibitor of Formula (I) or (II) of claims 1 and 10 or a pharmaceutically acceptable salt or solvate thereof.

* * * * *

UNITED STATES PATENT AND TRADEMARK OFFICE
CERTIFICATE OF CORRECTION

PATENT NO. : 7,560,449 B2 Page 1 of 1
APPLICATION NO. : 10/701244
DATED : July 14, 2009
INVENTOR(S) : Jay S. Fine et al.

It is certified that error appears in the above-identified patent and that said Letters Patent is hereby corrected as shown below:

Claim 2 at Column 32, line 48 replace "—$C_2$—" with -- —$CH_2$— --

Claim 2 at Column 33, line 1 replace "CONRR$^6$R$^7$" with -- CONR$^6$R$^7$ --

Signed and Sealed this

Fifteenth Day of June, 2010

David J. Kappos
*Director of the United States Patent and Trademark Office*